United States Patent
Serhuchev et al.

(10) Patent No.: US 7,470,827 B2
(45) Date of Patent: Dec. 30, 2008

(54) COMPOSITION FOR THE VAPOR PHASE DEHYDROHALOGENATION OF 1,1,2-TRIHALOETHANE TO 1,1-DIHALOETHYLENE AND METHODS FOR PREPARING AND USING SUCH COMPOSITION

(75) Inventors: Yurii Oleksiyovych Serhuchev, Kyiv (UA); Yurii Vasyliyovych Bilokopytov, Kyiv (UA); Igorlvanovych Chernobaev, Kyiv (UA)

(73) Assignee: PPG Industries Ohio, Inc., Cleveland, OH (US)

( * ) Notice: Subject to any disclaimer, the term of this patent is extended or adjusted under 35 U.S.C. 154(b) by 0 days.

(21) Appl. No.: 11/913,803

(22) PCT Filed: Jun. 3, 2005

(86) PCT No.: PCT/US2005/019709

§ 371 (c)(1),
(2), (4) Date: Apr. 30, 2008

(87) PCT Pub. No.: WO2006/132625

PCT Pub. Date: Dec. 14, 2006

(65) Prior Publication Data

US 2008/0242902 A1    Oct. 2, 2008

(51) Int. Cl.
C07C 17/00 (2006.01)
C07C 21/18 (2006.01)
(52) U.S. Cl. ............ 570/156; 570/155; 570/189
(58) Field of Classification Search .......... 570/155, 570/156, 189
See application file for complete search history.

(56) References Cited

U.S. PATENT DOCUMENTS

| | | |
|---|---|---|
| 5,210,344 A | 5/1993 | Reed et al. |
| 5,645,374 A | 7/1997 | Lesage et al. |
| 2005/0090697 A1 | 4/2005 | Webb |

FOREIGN PATENT DOCUMENTS

WO    9011131    4/1990

*Primary Examiner*—Jafar Parsa
(74) *Attorney, Agent, or Firm*—Frank Mallak

(57) ABSTRACT

Described are compositions adapted to catalyze the vapor phase dehydrohalogenation of 1,1,2-trihaloethane to 1,1-dihaloethylene, e.g., 1,1,2-trichloroethane to vinylidene chloride. These materials include activated carbon and at least one benzimidazole-containing material defined herein as including benzimidazole, a derivative thereof, a salt thereof or mixtures thereof. Also described are methods for producing and using these catalytic compositions.

24 Claims, 1 Drawing Sheet

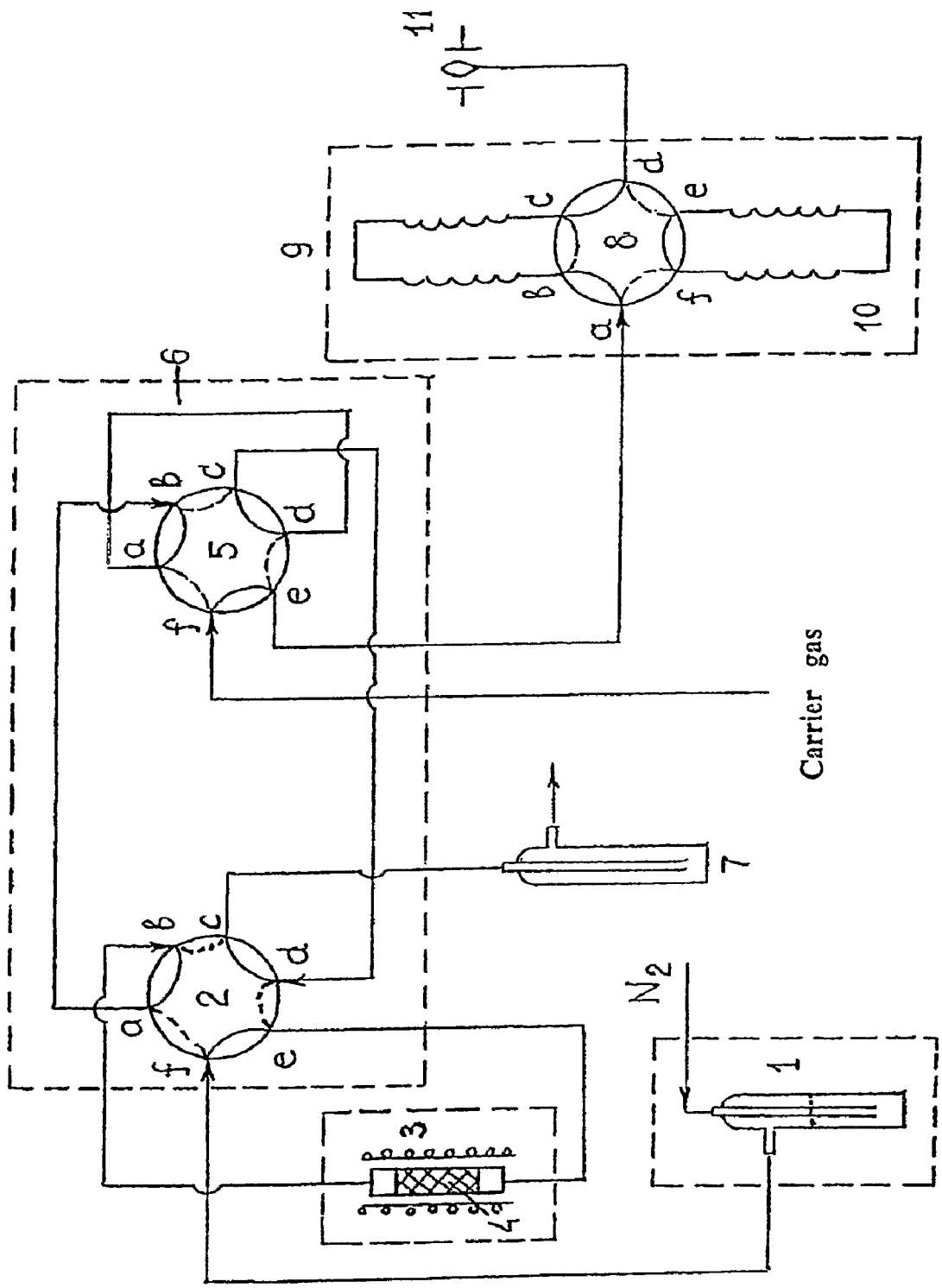
Fig.1. Scheme of experimental installation

COMPOSITION FOR THE VAPOR PHASE DEHYDROHALOGENATION OF 1,1,2-TRIHALOETHANE TO 1,1-DIHALOETHYLENE AND METHODS FOR PREPARING AND USING SUCH COMPOSITION

BACKGROUND OF THE INVENTION

The present invention relates to novel catalyst compositions that have been adapted to catalyze the dehydrohalogenation of 1,1,2-trihaloethane to 1,1-dihaloethylene, e.g., 1,1,2-tricholoroethane to 1,1-dichloroethylene that is also known as vinylidene chloride.

Various types of catalysts have been used in dehydrohalogenating applications. Although catalysts are known for this process, the use of the catalyst composition of the present invention has not been reported.

BRIEF DESCRIPTION OF THE FIGURE

FIG. 1 shows the scheme of the experimental installation used to process the Examples and Comparative Examples tested herein.

DESCRIPTION OF THE INVENTION

It is noted that, as used in this specification and the appended claims, the singular forms "a," "an," and "the" include plural referents unless expressly and unequivocally limited to one referent.

For the purposes of this specification, unless otherwise indicated, all numbers expressing quantities of ingredients, reaction conditions, and other parameters used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

In one non-limiting embodiment of the present invention, there is provided a catalytic composition comprising activated carbon and at least one material chosen from benzimidazole, a derivative thereof, salts thereof or mixtures thereof which hereinafter will be referred to as the "benzimidazole-containing material" in the specification and claims.

Activated carbons of the present invention in one non-limiting embodiment, can be any type of active carbon or activated charcoal. Conventional activated carbon is typically prepared by obtaining carbon by the destructive distillation of wood, e.g. birch, nut shells, kernels, e.g., seeds or grain, animal bones or other carbonaceous material and activating it by heating to 800 to 900° C. with steam or carbon dioxide. In addition to natural carbonaceous materials, synthetic carbon sources, as well as a variety of additives can be included to produce activated carbons having different properties, as known to those skilled in the art. See for example U.S. Patent Application 2004/0024074 and *Kirk-Othmer Encyclopedia of Chemical Technology*, Fourth edition, 1992, John Wiley & Sons pages 1015 to 1037, which disclosures are incorporated herein by reference.

In another non-limiting embodiment, the activated carbon is chosen from a synthetic activated carbon, e.g., spherical activated carbon, comprising from 1 to 8 weight percent of nitrogen. Such synthetic activated carbons are produced by including a nitrogen source in the preparation process. Methods for producing spherical activated carbon are disclosed in U.S. Patent Application 2004/0024074.

In a further non-limiting embodiment, the activated carbon of the present invention comprises a specific surface area that can vary widely. In alternate non-limiting embodiments, it can range from 250-2,000 meters squared per gram ($m^2/g$), from 400 to 1800 $m^2/g$ or from 1000 to 1510 $m^2/g$. The specific surface area of the activated carbon in the catalyst composition of the present invention can range between any combination of these values, inclusive of the recited range, e.g., from 251 to 1999 $m^2/g$.

In a still further non-limiting embodiment, the pore size of the activated carbon can vary widely. According to the IUPAC classification system, pore sizes are subdivided into micropores having a pore diameter of less than 2 nanometers (nm), mesopores having a pore diameter of from 2-50 nanometers and macropores having a pore diameter of greater than 50 nm. It has been calculated that the diameter of the benzimidazole-containing material is about 2 nm.

In one non-limiting embodiment, the activated carbon in the composition of the present invention comprises a proportion of micropores, mesopores and macropores that enable the dehydrohalogenating of 1,1,2-trihaloethane to 1,1-dihaloethylene by benzimidazole-containing material. In another non-limiting embodiment, the activated carbon in the catalyst composition of the present invention comprises substantially mesopores and macropores. In a further non-limiting embodiment, the activated carbon has a pore size equal to or greater than 2 nanometers. In a still further non-limiting embodiment, the activated carbon comprises a pore size from 2-50 nanometers.

A benzimidazole derivative is defined herein as a material formed by the addition of at least one substituent to benzimidazole. Non-limiting examples of benzimidazole derivatives include the materials described hereinafter listed as materials a) to r) and the materials represented by graphic formulae I through V, salts thereof and mixtures thereof.

In another non-limiting embodiment, the benzimidazole-containing material of the present invention comprises an acidity constant (pKa) in acetonitrile that can vary widely. The pKa is measured by means within the skill in the art such as the methods described by Ivari Kaljurand, et al., "Self-Consistent Spectrophotometric Basicity Scale In Acetonitrile Covering the Range Between Pyridine and DBU," J. Org. Chem, 2000, 65, 6202-6208, which disclosure is incorporated herein by reference.

In one non-limiting embodiment, the pKa of the benzimidazole-containing material in acetonitrile can be at least 10.0. In another non-limiting embodiment, the pKa can be at least 11.0. In a further non-limiting embodiment, the pKa can be at least 18.0. In a still further non-limiting embodiment, the pKa of the benzimidazole-containing material can be higher than 18. In one non-limiting embodiment, the pKa is usually 18.0 or less. The acidity constant of the benzimidazole-containing material of the present invention can range between any combination of the values given, inclusive of the recited range, e.g., an acidity constant of from 10.1 to 18.1.

The effects of specific substituents on the acidity constant of benzimidazole-containing materials is known to those skilled in the art. See *Benzimidazole and Congeneric Tricyclic Compounds Part 1*, edited by P. N. Preston, John Wiley & Sons, 1981, pages 79-82 and M. T. Davies et al "The Chemistry of Anti-Pernicious Anemia Factors, Part VIII The Basicity of Some Benzimidazoles and Benzimidazole Glycosides", J. Pharm. Pharmacol. (1951) 3, pages 420-430; *Comprehensive Heterocyclic Chemistry*, edited by Kevin T. Potts, Pergamon Press, 1984, pages 345 to 497; and the aforementioned article by Ivari Kaljurand, et al.

In alternate non-limiting embodiments, the types of salts of the benzimidazole and the benzimidazole derivatives of the present invention can vary widely as known to those skilled in the art. Non-limiting examples include: hydrohalogenides such as hydrofluoride, hydrochloride, hydrobromide and hydroiodide; perchlorates; sulfates; phosphates; carbonates; $C_1$-$C_6$ alkylsulfonates, which are optionally substituted with fluorines, such as methanesulfonate, trifluoromethanesulfonate, ethanesulfonate, pentafluoroethanesulfonate, propanesulfonate, butanesulfonate, pentanesulfonate and hexanesulfonate; $C_6$-$C_{10}$ arylsulfonates such as benzenesulfonate and p-toluenesulfonate; carboxylic acid salts such as acetate, propionate, butyrate, benzoate, fumarate, maleate, succinate, citrate, tartarate, oxalate and malonate; and amino acid addition salts such as glutamate and aspartate. In another non-limiting embodiment, the salts of this invention include hydrates and solvates of organic solvents.

In another non-limiting embodiment, the benzimidazole-containing material is represented by at least one of the following graphic formulae, salts thereof or mixtures thereof:

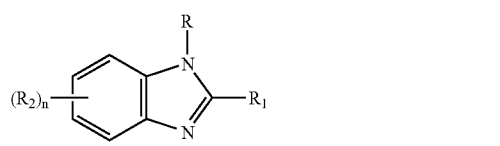

I

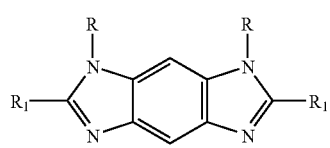

II

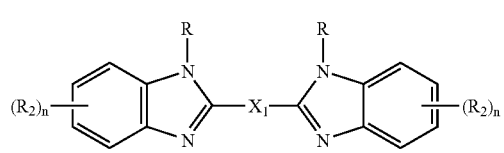

III

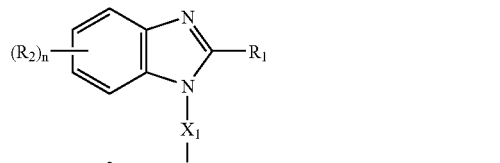

IV

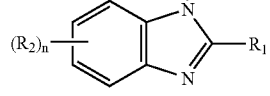

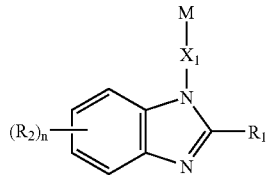

V wherein:

(a) R is chosen from hydrogen, $C_1$-$C_6$ alkyl, $C_1$-$C_6$ haloalkyl, $C_1$-$C_6$ alkoxy($C_1$-$C_4$)alkyl, $C_3$-$C_6$ cycloalkyl, mono($C_1$-$C_6$)alkoxy($C_3$-$C_6$)-cycloalkyl, mono($C_1$-$C_6$)alkyl ($C_3$-$C_6$)cycloalkyl, halo($C_3$-$C_6$)cycloalkyl, —N($R_4$)$R_5$, —($C_1$-$C_6$)alkylene-N($R_4$)$R_5$ or —($C_1$-$C_6$)alkylene-oxy-N($R_4$)$R_5$, wherein $R_4$ and $R_5$ are each independently chosen for each occurrence from hydrogen, $C_1$-$C_6$ alkyl, $C_1$-$C_6$ alkoxy, $C_5$-$C_7$ cycloalkyl, $C_6$-$C_{20}$ bicycloalkyl, $C_7$-$C_{20}$ tricycloalkyl, mono($C_1$-$C_6$)alkylamino($C_1$-$C_6$)alkylene, di($C_1$-$C_6$)alkylamino($C_1$-$C_6$)alkylene, aryl, furanyl, thienyl, $C_1$-$C_6$ alkoxyalkyl, mono-substituted and di-substituted aryl, or $R_4$ and $R_5$ together with the nitrogen atom form an unsubstituted, mono-substituted or di-substituted heterocyclic ring chosen from pyridyl, quinolyl, isoquinolyl, indolinyl, morpholino, pyrimidinyl, piperidino, pyrrolidyl, imidazolidyl, imidazolinyl, pyrazolidyl, pyrazolinyl, piperazinyl, pyrryl, $C_6$-$C_{20}$ heterobicycloalkyl or, $C_7$-$C_{20}$ heterotricycloalkyl, each of said aryl and heterocyclic ring substituents being chosen from halo, amino, mono($C_1$-$C_6$)alkylamino, di($C_1$-$C_6$)alkylamino, amino($C_1$-$C_6$)alkylene, mono($C_1$-$C_6$)alkylamino($C_1$-$C_6$)alkylene, di($C_1$-$C_6$)alkylamino($C_1$-$C_6$)alkylene, $C_1$-$C_6$ alkyl or $C_1$-$C_6$ alkoxy;

(b) $R_1$ is chosen from:

(i) hydrogen, $C_1$-$C_6$ alkyl, $C_1$-$C_6$ haloalkyl, $C_1$-$C_6$ alkoxy ($C_1$-$C_6$)alkyl, $C_1$-$C_6$ alkyl($C_1$-$C_6$)alkoxy, aryloxy($C_1$-$C_6$)alkyl, aryl($C_1$-$C_6$)alkyl, haloaryl($C_1$-$C_6$)alkyl, aryl ($C_1$-$C_6$)alkoxy, haloaryl($C_1$-$C_6$)alkoxy, $C_3$-$C_6$ cycloalkyl, mono($C_1$-$C_6$)alkoxy($C_3$-$C_6$)cycloalkyl, mono($C_1$-$C_6$)alkyl($C_3$-$C_6$)cycloalkyl, halo($C_3$-$C_6$)cycloalkyl, —($C_1$-$C_6$)alkylene-N($R_4$)$R_5$, —($C_1$-$C_6$)alkylene-oxy-N($R_4$)$R_5$ or —N($R_4$)$R_5$; or (ii) unsubstituted, mono-, di-, or tri-substituted aryl groups, phenyl or naphthyl, each of said aryl substituents being chosen from —N($R_4$)$R_5$, hydroxy, aryl, mono($C_1$-$C_6$) alkoxyaryl, di($C_1$-$C_6$)alkoxyaryl, mono($C_1$-$C_6$)alkylaryl, $C_1$-$C_6$ alkoxy ($C_1$-$C_6$)alkoxy, di($C_1$-$C_6$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_6$)alkyl, $C_3$-$C_7$ cycloalkyloxy($C_1$-$C_6$)alkoxy, aryl($C_1$-$C_6$)alkyl, aryl($C_1$-$C_6$)alkoxy, aryloxy, aryloxy($C_1$-$C_6$)alkyl, aryloxy($C_1$-$C_6$)alkoxy, mono- or di-($C_1$-$C_6$)alkylaryl($C_1$-$C_6$)alkyl, mono- or di-($C_1$-$C_6$)alkoxyaryl($C_1$-$C_6$)alkyl, mono- or di-($C_1$-$C_6$)alkylaryl($C_1$-$C_6$)alkoxy, mono- or di-($C_1$-$C_6$)alkoxyaryl($C_1$-$C_6$)alkoxy, $C_1$-$C_6$ alkyl, $C_1$-$C_6$ haloalkyl, $C_1$-$C_6$ alkoxy, mono($C_1$-$C_6$)alkoxy ($C_1$-$C_4$)alkyl, halogen, —$SR_3$, or —$S(O)R_3$,; wherein $R_3$ is chosen from —N($R_4$)$R_5$, $C_1$-$C_6$ alkyl, phenyl($C_1$-$C_3$)alkyl, mono($C_1$-$C_6$)alkyl substituted phenyl($C_1$-$C_3$) alkyl, mono($C_1$-$C_6$)alkoxy substituted phenyl($C_1$-$C_3$) alkyl or an unsubstituted, mono- or di-substituted aryl group wherein each of said aryl group substituents of $R_3$ being independently chosen from —N($R_4$)$R_5$, $C_1$-$C_6$ alkyl or $C_1$-$C_6$ alkoxy;

(c) each $R_2$ is independently chosen for each occurrence from: R or $R_1$ and n is the integer 0, 1, 2, 3 or 4;

(d) $X_1$ is chosen from —$(CH_2)_t$—; —O—$(CH_2)_t$—; or —O—$(CH_2)_t$—O—; wherein t is the integer 1, 2, 3, 4, 5 or 6; or the group T represented by the formula:

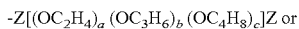

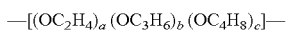

wherein -Z is —C(O)— or —$CH_2$—, a, b and c are each a number between 0 and 50, and the sum of a, b and c is between 2 and 50; and x and y are each independently chosen for each occurrence from 2, 3 or 4; and (e) M is chosen from hydroxy, methacryloxy, acryloxy, 2-(methacryloxy)ethylcarbamyl, 2-(acryloxy)ethylcarbamyl, epoxy, vinyl, allyl or tri($C_1$-$C_6$)alkoxysilyl.

In a further non-limiting embodiment, the benzimidazole-containing material is represented by at least one of the following graphic formulae or mixtures thereof:

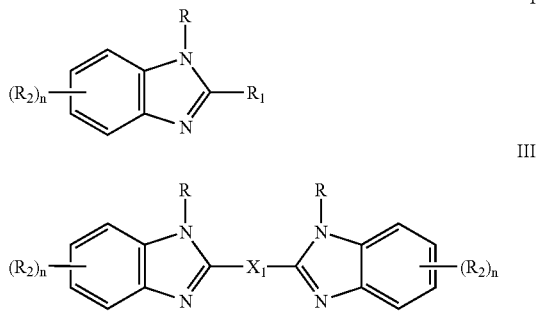

wherein:

(a) R is chosen from hydrogen, $C_1$-$C_6$ alkyl, $C_1$-$C_6$ haloalkyl, halo($C_3$-$C_6$)cycloalkyl, —N($R_4$)$R_5$, —($C_1$-$C_6$) alkylene-N($R_4$)$R_5$ or —($C_1$-$C_6$)alkylene-oxy-N($R_4$)$R_5$, wherein $R_4$ and $R_5$ are each independently chosen for each occurrence from hydrogen, $C_1$-$C_6$ alkyl, mono($C_1$-$C_6$)alkylamino($C_1$-$C_6$)alkylene, di($C_1$-$C_6$)alkylamino($C_1$-$C_6$)alkylene, aryl, furanyl, thienyl, mono-substituted or di-substituted aryl, or $R_4$ and $R_5$ together with the nitrogen atom form an unsubstituted or mono-substituted heterocyclic ring chosen from pyridyl, quinolyl, isoquinolyl, morpholino or piperidino, each of said aryl and heterocyclic ring substituents being chosen from halo, amino, mono($C_1$-$C_6$)alkylamino, di($C_1$-$C_6$)alkylamino, amino($C_1$-$C_6$)alkylene, mono($C_1$-$C_6$)alkylamino($C_1$-$C_6$)alkylene, di($C_1$-$C_6$)alkylamino($C_1$-$C_6$)alkylene, $C_1$-$C_6$ alkyl or $C_1$-$C_6$ alkoxy;

(b) $R_1$ is chosen from:
(i) hydrogen, $C_1$-$C_6$ alkyl, $C_1$-$C_6$ haloalkyl, aryloxy($C_1$-$C_6$) alkyl, halo($C_3$-$C_6$)cycloalkyl, —($C_1$-$C_6$)alkylene-N($R_4$)$R_5$, —($C_1$-$C_6$)alkylene-oxy-N($R_4$)$R_5$ or —N($R_4$)$R_5$; or
(ii) unsubstituted, mono-, or di-substituted aryl groups, phenyl or naphthyl, each of said aryl substituents being chosen from —N($R_4$)$R_5$, aryl, mono($C_1$-$C_6$)alkoxyaryl, di($C_1$-$C_6$)alkoxyaryl, mono($C_1$-$C_6$)alkylaryl, di($C_1$-$C_6$) alkylaryl, haloaryl, $C_3$-$C_7$ cycloalkylaryl, aryloxy, $C_1$-$C_6$ alkyl, $C_1$-$C_6$ haloalkyl, $C_1$-$C_6$ alkoxy, halogen, or —$SR_3$; wherein $R_3$ is chosen from —N($R_4$)$R_5$, $C_1$-$C_6$ alkyl, or an unsubstituted, or mono-substituted aryl group wherein each of said aryl group substituents of $R_3$ being independently chosen from —N($R_4$)$R_5$, $C_1$-$C_6$ alkyl or $C_1$-$C_6$ alkoxy;

(c) each $R_2$ is independently chosen for each occurrence from: R or $R_1$ and n is the integer 0, 1, 2 or 3;

(d) $X_1$ is chosen from —$(CH_2)_t$—; wherein t is the integer 1, 2, 3, 4, 5 or 6.

In a still further non-limiting embodiment the benzimidazole-containing materials and mixtures thereof are represented by graphic formulae I and III wherein:

(a) R is chosen from hydrogen, $C_1$-$C_3$ alkyl, $C_1$-$C_3$ haloalkyl, or —N($R_4$)$R_5$, wherein $R_4$ and $R_5$ are each independently chosen for each occurrence from hydrogen or $C_1$-$C_3$ alkyl or $R_4$ and $R_5$ together with the nitrogen atom form an unsubstituted or mono-substituted heterocyclic ring chosen from pyridyl, quinolyl, isoquinolyl, morpholino or piperidino, each of said aryl and heterocyclic ring substituents being chosen from chloro, fluoro, amino, mono($C_1$-$C_3$)alkylamino, or di($C_1$-$C_3$)alkylamino;

(b) $R_1$ is chosen from:
(i) hydrogen, $C_1$-$C_3$ alkyl, $C_1$-$C_3$ haloalkyl, halo($C_3$-$C_6$) cycloalkyl, phenoxy ($C_1$-$C_3$) alkyl, naphthoxy($C_1$-$C_3$) alkyl, —($C_1$-$C_3$)alkylene-N($R_4$)$R_5$, —($C_1$-$C_3$)alkylene-oxy-N($R_4$)$R_5$ or —N($R_4$)$R_5$; or
(ii) unsubstituted, or mono-substituted aryl groups, phenyl or naphthyl, each of said aryl substituents being chosen from —N($R_4$)$R_5$, aryl, $C_1$-$C_3$ alkyl, $C_1$-$C_3$ haloalkyl, $C_1$-$C_3$ alkoxy, chloro or fluoro;

(c) each $R_2$ is independently chosen for each occurrence from: R or $R_1$ and n is the integer 0, 1 or 2; and (d) $X_1$ is chosen from —$(CH_2)_t$—; wherein t is the integer 1, 2 or 3.

In a further non-limiting embodiment of the present invention, the benzimidazole-containing material can be chosen from:
a) 2-phenylbenzimidazole;
b) 2-(4-chlorophenyl)benzimidazole;
c) 2-(4-chlorophenyl)-1-methylbenzimidazole;
d) 1-methyl-2-(4-methoxyphenyl)benzimidazole;
e) 1,2,4,5-bis(methylimidazo)benzene;
f) 2-(4-tolyl)benzimidazole;
g) 2-(4-pyridyl)benzimidazole;
h) 2-ethyl-1-methylbenzimidazole;
i) 1-methyl-2-(4-tolyl)benzimidazole;
j) 2-methylbenzimidazole;
k) bis(2-benzimidazolyl)methane;
l) 1,2,4,5-bis(methylimidazo)benzene;
m) benzimidazole;
n) 2-(phenoxymethyl)benzimidazole;
o) 2-(2-naphthoxymethyl)benzimidazole;
p) 2-(4-dimethylaminophenyl)benzimidazole;
q) salts thereof; or
r) mixtures thereof.

Methods for the preparation of the substituted benzimidazoles represented by graphic formula I are well known to those skilled in the art. For example, 2-aminomethylbenzimidazole can be prepared by reacting o-phenylene diamine and aminoacetic acid in equimolar amounts in the presence of hydrochloric acid and 2-methylbenzimidazole can be prepared by the reaction of o-phenylene diamine with acetic acid in an aqueous solution of hydrochloric acid. See, also, the procedures described in *Comprehensive Organic Chemistry. The Synthesis and Reactions of Organic Compounds*, edited by D. Barton and W. D. Ollis, vol 4, "Heterocyclic Compounds", Pergamon Press, Oxford, 1979; P. N. Preston "Synthesis, Reactions, and Spectroscopic Properties of Benzimidazoles", Chem. Rev., 1974, 74 No. 3, pp. 279-314; and in *Benzimidazoles and Congeneric Tricyclic Compounds Part 1*, cited hereinbefore.

Methods for the preparation of materials represented by graphic formula II are well known to those skilled in the art. See Cemil Ogretir and Seref Demirayak "Benzimadazole Studies v. Synthesis and Proton-Gain, Proton-Loss Behaviors of Some [Benzo 1,2-d, 4,5-d] Diimidazoles and Their Hammett Relationships", Chimica Acta Turcica 14, 1986, pp. 285-298.

Methods for the preparation of materials represented by graphic formula III are well known to those skilled in the art. See the aforecited article by P. N. Preston in Chem. Rev., Section II H, "Synthesis of Bibenzimidazolyls and Related Compounds", p. 288.

Methods for the preparation of materials represented by graphic formula IV are well known to those skilled in the art such as by the Chichibabin reaction in which heterocyclic nitrogen compounds are aminated with alkali-metal amides. See *Comprehensive Heterocyclic Chemistry*, edited by Kevin T. Potts, Vol. 5, Part 4A, 1984, pp. 409-412 and 459-460 and U.S. Pat. No. 5,414,010, at column 7, line 50 to column 18, line 15.

Methods for the preparation of materials represented by graphic formula V are well known to those skilled in the art. In one non-limiting embodiment, the methods disclosed for the preparation of material represented by graphic formula I can be used along with known methods to convert or replace the —R substituent with an —$X_1$-M substituent.

In one non-limiting embodiment, the composition of the present invention can be used for dehydrohalogenating 1,1,2-trihaloethane to dihaloethylene, e.g., 1,1,2-trichloroethane to 1,1-dichloroethylene, 1,1,2-tribromoethane to 1,1-dibromoethylene, 1,1,2-trifluoroethane to 1,1-difluoroethylene, 1,1,2-triiodoethane to 1,1-diiodoethylene. In another non-limiting embodiment, the dehydrohalogenation method of the present invention is conducted in suitable process equipment which includes fixed, moving or fluidized bed reactors known to those skilled in the art. See U.S. Pat. No. 5,246,903 at column 7, lines 2 to 48 and U.S. Pat. No. 4,144,192 at column 2, line 43 to column 3, line 7, which disclosures are incorporated herein by reference.

In a further non-limiting embodiment, 1,1,2-trihaloethane is dehydrohalogenated to dihaloethylene by a method comprising:
 a) obtaining an activated carbon comprising a catalytic amount of at least one benzimidazole-containing material;
 b) obtaining a vapor phase of 1,1,2-trihaloethane; and
 c) contacting (a) with (b) to form reaction products comprising 1,1-dihaloethylene.

In another non-limiting embodiment, the method further comprises (d) recovering 1,1-dihaloethylene from (c). Methods for the recovery of halogenated hydrocarbons are known to those skilled in the art. One non-limiting embodiment is by distilling the products of the reaction through a fractionating column and drawing off the desired fraction.

In a still further non-limiting embodiment, the vapor phase of 1,1,2-trihaloethane and a non-reactive diluent is contacted with a catalyst comprising a catalytic amount of at least one benzimidazole-containing material and activated carbon at an elevated temperature, for a time sufficient to cause a conversion of 1,1,2-trihaloethane to reaction products that comprise substantially 1,1-dihaloethylene.

In one non-limiting embodiment, a catalytic amount of the benzimidazole-containing material associated with the activated carbon is an amount that causes the dehydrohalogenation of 1,1,2-trihaloethane to 1,1-dihaloethylene with greater selectivity for 1,1-dihaloethylene, e.g. vinylidene chloride, than would occur if the benzimidazole-containing material was not associated with the activated carbon. In another non-limiting embodiment, the catalytic amount can range from 1 to 40 weight percent, or from 2 to 35 weight percent, or from 5 to 30 weight percent, or from 10 to 20 weight percent, inclusive of ranges of all numbers within these ranges, e.g. from 1.5 to 39.5 weight percent, the weight percent being based on the increase in weight of the activated carbon due to the benzimidazole-containing material measured after drying, divided by the weight of the activated carbon and multiplied by 100, as described in Example Preparation herein.

In a still further non-limiting embodiment, the temperature at which the vapor phase of 1,1,2-trihaloethane is maintained can vary widely. In one non-limiting embodiment, the temperature at which the vapor phase is maintained is the temperature at which the 1,1,2-trihaloethane boils. In alternate non-limiting embodiments, the vapor phase of 1,1,2-trihaloethane can be maintained at a temperature of from 114 to 300° C., from 150 to 285° C., from 200 to 260° C., or from 215 to 260° C. The temperature at which the vapor phase of 1,1,2-trihaloethane can be maintained for the process of the present invention can range between any combination of these values, inclusive of the recited range, e.g., from 114.1-299.9° C.

In a still further non-limiting embodiment the time for contacting the catalyst composition of the present invention with the vapor phase of 1,1,2-trihaloethane can vary widely. In one non-limiting embodiment, it can range from 0.1 to 3,600 seconds and any inclusive range, e.g. from 10 to 1,000 seconds. Stated another way, the space velocity, measured as the volume of 1,1,2-trihaloethane vapor passing through a given volume of catalyst space in unit time, can vary widely. In alternate non-limiting embodiments, it can vary from 1 to 30,000 per hour ($h^{-1}$), 5 to 10,000 ($h^{-1}$), 10 to 5,000 ($h^{-1}$), 30 to 1,500 ($h^{-1}$), from 60 to 1,300 $h^{-1}$, from 80 to 1,200 $h^{-1}$, from 100 to 1,100 $h^{-1}$ or from 200 to 800 $h^{-1}$. The space velocity at which the vapor phase of 1,1,2-trihaloethane can be maintained for the process of the present invention can range between any combination of these values, inclusive of the recited range, e.g., from 1.1 to 29,999.9 $h^{-1}$.

In one non-limiting embodiment, the concentration of 1,1,2-trihaloethane in the vapor phase processed by the method of the present invention can vary widely. In another non-limiting embodiment, the vapor phase of 1,1,2-trihaloethane can be mixed with a non-reactive diluent, e.g., another vapor or gas phase as known to those skilled in the art. Non-limiting examples of volatile liquids that could be used to produce a vapor phase for use with or without nitrogen include non-halogenated organic solvents such as cyclohexene, cyclohexane, benzene, toluene, methanol, hexane, dioxane, pentane, petroleum ethers or mixtures thereof. In one non-limiting embodiment, the vapor or gas can be nitrogen or any other gaseous material that would not interfere with the dehydrohalogenation process, e.g., inert gases such as argon or helium. In a further non-limiting embodiment the vinyl halide byproduct of the dehydrohalogenation process or mixtures with the aforementioned vapors and gases could be used as a diluent for 1,1,2-trihaloethane. In another non-limiting embodiment, the volume ratio of the vapor phase of 1,1,2-trihaloethane to the other vapor or gas phase can vary widely when such a diluent is used. In a further non-limiting embodiment, the volume ratio of the vapor phase of 1,1,2-trihaloethane to the diluent vapor or gas phase can range from 1:99 to 99:1 and any ratio within this range.

In one non-limiting embodiment, the composition of the present invention can be prepared by the following method comprising:
 a) obtaining an activated carbon; and
 b) introducing at least one benzimidazole-containing material into said activated carbon.

In a further non-limiting embodiment, the aforedescribed method of the present invention further comprises dissolving the at least one benzimidazole-containing material in a solvent prior to introducing it into the activated carbon. In one non-limiting embodiment, a suitable solvent is one in which the benzimidazole-containing material at least partially dissolves.

In a still further nonlimiting embodiment the solvent can vary widely as known by those skilled in the art. Non-limiting examples include water, acetone, acetonitrile, ethanol, propanol, methylene chloride, n-methylpyrrolidinone, dioxane, chloroform, nitromethane, benzene, toluene, methyl ethyl ketone, methyl isobutyl ketone, isopropyl alcohol, propylene carbonate, 2-methoxyethyl ether, xylene, cyclohexane, 3-methyl cyclohexanone, ethyl acetate, butyl acetate, tetrahydrofuran, amyl propionate, methyl propionate, propylene glycol methyl ether, dimethyl sulfoxide, dimethyl formamide, diethylene glycol dibenzoate, dialkyl ethers of ethylene glycol, e.g., diethylene glycol dimethyl ether and their derivates (sold as CELLOSOLVE industrial solvents) or mixtures thereof.

The present invention is more particularly described in the following examples which are intended as illustration only, since numerous modifications and variations therein will be apparent to those skilled in the art.

EXAMPLE 1

Part A—Preparation of Benzimidazole Derivatives

The following Benzimidazole Derivatives (BD) were prepared as follows:

BD-A

A mixture of o-di(benzamido)benzene (150 grams (g)), potash (50 g) and ethylene glycol (100 milliliters (mL)) was added to a reaction flask equipped with a mixer and cooling mantle, was heated to the reflux temperature. After cooling to room temperature, the stirred reaction mixture was diluted with water. The product was filtered, washed with water and ethanol, and purified by crystallization from ethanol. A Nuclear Magnetic Resonance (NMR) spectrum showed the product to have a structure consistent with 2-phenylbenzimidazole.

BD-B

A mixture of p-chlorobenzoic acid (3.5 g), o-phenylenediamine (2.4 g), boric acid (0.15 g) and dimethylaniline (10 mL) was added to a reaction flask and heated, under a flow of nitrogen, in an oil bath at 195-205° C. for 3 hours. After cooling to room temperature, the resulting mixture was stirred with water (15 mL) and concentrated $NH_4OH$ (2 mL) and filtered. The solid product was washed with water and toluene and dried at 60-80° C. An NMR spectrum showed the product to have a structure consistent with 2-(4-chlorophenyl)benzimidazole.

BD-C

A mixture of 2-(4-chlorophenyl)benzimidazole (17.1 g, 0.075 mole), crushed KOH (12.6 g, 0.225 mole and DMSO (40 mL) was added to a reaction flask and stirred for 20 minutes at 20-25° C. Methyl iodide (7.0 mL, 0112 mole) was added dropwise over a period of 20 minutes, the thickened mixture was diluted with water. The product was filtered, washed with water, squeezed, vacuum filtered, and dried at 60-80° C. yielding 17.84 g (98.3%). An NMR spectrum showed the product to have a structure consistent with 2-(4-chlorophenyl)-1-methylbenzimidazole.

BD-D

A mixture of o-phenylenediamine (21.6 g, 0.2 mole), p-nitrobenzaldehyde (30.2 g, 0.2 mole) and morpholine (3.0 mL) was boiled in a flask without a condenser for 3 hours and allowed to stand overnight. The resulting crystalline product was filtered, washed with dimethylforamide (DMF) and benzene, and recrystallized from DMF. Yellow shiny crystals having a melting point (mp) 305-310° C. were recovered. An NMR spectrum showed the product to have a structure consistent with 2-(4-nitrophenyl)benzimidazole.

BD E

2-Aminomethylbenzimidazole.

BD-F

A mixture of 2-(4-hydroxyphenyl)benzimidazole (13.7 g) and crushed KOH (22.0 g) in DMSO (60 mL) was added to a reaction flask and stirred at 20-25° C. for 10 minutes. Methyl iodide (12.2 g) was added dropwise over a period of 20 minutes while cooling the flask in a water bath. The resulting mixture was diluted with water (150 mL). The resulting precipitate was filtered, washed with water, vacuum filtered, and dried at about 60° C. The product was purified by dissolving it in boiling water, in the presence of concentrated HCl (10 mL). An NMR spectrum showed the product to have a structure consistent with 1-methyl-2-(4-methoxyphenyl)benzimidazole.

BD-G

2-Methylbenzimidazole was nitrated with a mixture of nitric and sulfuric acid, first to the mono-nitro product and then to 2-methyl-5,6-dinitrobenzimidazole. The latter was reduced with tin in aqueous HCl to 5,6-diamino-2-methylbenzimidazole after decomposition of the intermediate organotin product with hydrogen sulfide. The resulting diamine was converted into 1,2,4,5-bis(methylimidazo)benzene dihydrochloride by heating with acetic acid in aqueous HCl in an autoclave, for 1 hour at 180° C. The salt was purified by reprecipitation through the free base and its salt with acetic acid yielding 40% of the product. An NMR spectrum showed the product to have a structure consistent with 1,2,4,5-bis(methylimidazo)benzene.

Part B—Preparation of BD Carriers

Synthetic activated carbons in the form of spherically granulated carbonite were prepared from a nitrogen-containing co-polymer by pyrolysis and subsequent high temperature activation as described in U.S. Patent Application 2004/0024074. The spherical activated carbon materials were obtained from V. V. Strelko, Institute Absorption and Endoecology National Academy of Sciences of Ukraine and Kiev. Different grades having different levels of nitrogen, were used in the Examples. Listed below are the approximate nitrogen levels in the different grades of synthetic activated carbons tested.

| Grades | Nitrogen Level |
| --- | --- |
| SKN-M | about 4% |
| SKN-3M | about 2% |
| SKN-1K | About 1% |

The specific surface areas of the above synthetic activated carbon supports range from 420-1,520 m²/g. SKN-M had a specific surface area of approximately 1,000 m²/g.

Birch Activated Carbon having a specific surface area of from 800-1,000 m²/g that was commercially available in the former USSR was used.

Kernel Activated Carbon having a specific surface area of from 800-1,000 m²/g that was commercially available in the former USSR was used.

The silica gel grade KSS from the Experimental Plant of the Research Institute of Petroleum Processing Industry, Nizhnii Novgorod, Russia with a specific surface area of 520 m²/g was used for the Comparative Example.

Part C—General Example Preparation

Samples of activated carbons and silica gel were each saturated with a solution containing the Benzimidazole Derivatives as a free base or hydrochloride salt in acetone, acetonitrile or a mixture thereof and kept in a closed container at room temperature for 12 to 24 hours. Afterwards, it was dried, in an oven at 100° C. for three hours. The weight percent reported for each example is based on the increase in weight of the support due to the Benzimidazole Derivatives measured after drying divided by the weight of the support and multiplied by 100.

Part D—Preparation of Example 1

20 Weight percent of BD-A on SKN-1K. Results are presented in Table 1.

EXAMPLE 2

30 Weight percent of BD-A on SKN-1K. Results are presented in Table 2.

EXAMPLE 3

35 Weight percent of BD-A on SKN-3M. Results are presented in Table 3.

EXAMPLE 4

30 Weight percent of BD-A on SKN-M. Results are presented in Table 4.

EXAMPLE 5

20 Weight percent of BD-A on Birch Active Carbon. Results are presented in Table 5.

EXAMPLE 6

20 Weight percent of BD-A on Kernel Active Carbon. Results are presented in Table 6.

EXAMPLE 7

5 Weight percent of BD-B on SKN-M. Results are presented in Table 7.

EXAMPLE 8

10 Weight percent of BD-B on SKN-M. Results are presented in Table 8.

EXAMPLE 9

20 Weight percent of BD-B on SKN-M. Results are presented in Table 9.

EXAMPLE 10

25 Weight percent of BD-B on SKN-M. Results are presented in Table 10.

EXAMPLE 11

20 Weight percent of BD-C on SKN-M. Results are presented in Table 11.

EXAMPLE 12

20 Weight percent of BD-D on SKN-M. Results are presented in Table 12.

EXAMPLE 13

20 Weight percent of BD-E on SKN-M. Results are presented in Table 13.

EXAMPLE 14

20 Weight percent of BD-F on SKN-M. Results are presented in Table 14.

EXAMPLE 15

20 Weight percent of BD-G on SKN-M. Results are presented in Table 15.

EXAMPLE 16

30 Weight percent of BD-G on SKN-M. Results are presented in Table 16.

COMPARATIVE EXAMPLE 1

20 Weight percent of BD-A a silica gel grade KSS. Results are presented in Table 17.

COMPARATIVE EXAMPLE 2

SKN-M tested without Benzimidazole derivatives. Results are presented in Table 18.

EXAMPLE 17

Part A—Testing Equipment

Examples, 1-16 and Comparative Examples 1 and 2 were tested in the flow type apparatus shown by FIG. 1. Five cubic centimeters of the sample was loaded into a stainless steel reactor (3) measuring 12.0 centimeters by 0.6 centimeters. The reactor was heated to the temperature indicated in the tables and was controlled to within ±0.3 degrees C.

The flow of nitrogen gas was initiated through a saturator (1) containing trichlorethylene and was directed through the six way valve (2)(f→e) to reactor 3 filled with the Examples or Comparative Examples (4). The concentration of TCE which represents trichlorethylene in the feed gas was controlled by changing the temperature of the saturator (1). The reaction products were emitted through the valve (2)(b→a), to the six way sampling valve(5). The outlets (a) and (d) of valve (5) were connected with a metal tube (6), the capacity of which determines the size of the sample. With the valve (5) in a position indicated by solid lines, the products, having passed the way b→a→d→c, filled the tube (6) (a→d) and entered, through valve (2)(c→d), the receiver (7). At the same time, the carrier gas, nitrogen, via the valve (5)(f→e) and the six way valve (8)(a→b), was directed to the chromatographic column (9) and then passed to the modified Flame Ionization Detector (FID) having a detection limit of $1 \times 10^{-9}$ mole which was built into the chromatograph LKhW-8MD.

With valve (5) in the position indicated by broken lines, the products passed via valves (5)(b→c) and (2)(d→c), to the receiver (7). The carrier gas traversed the path f→a→d→e and transported the reaction products from the tube (6) to the column (9). The capacity of the tube (a→d) and its connectors was 0.906 mL at 150° C. All the valves and fittings were maintained at the indicated temperature to avoid condensation of the products.

With valve (2) in the position indicated by broken lines, the starting reaction mixture was fed into the reactor (3) via (2)(f→a), (5)(b→a→d→c) and then via (2)(d→e). The products in this case passed through valve (2)(b→c) and arrived at the receiver (7).

Thus, with the valve (2) in the position indicated by solid lines, the effluents from the reactor were directed via valve (2)(b→a) to (5)(b→e) to (8)(a→b) to the chromatographic column (a). In the alternative position of valve (2) (broken lines), the starting reaction mixture was directed to the chromatographic column and analyzed. The samples of the starting mixture and the reaction products to be analyzed were the identical size and the relative error of the measurements was the same in all of the experiments.

Part B—Identification/Characterization of the Reagents Used

The 1,1,2-trichloroethane (TCE) was of 99.5% purity was used as received from the supplier. The identification of the reaction products and the calibration of the Flame Ionization Detector (FID) were performed with model mixtures of pure compounds (vinyl chloride (VC), vinylidene chloride (VDC), trans- and cis-1,2-dichloroethylene (trans-DCE) and (cis-DCE) that were prepared as follows:

1. Vinylidene chloride was obtained by dehydrochlorination of TCE with an aqueous solution of calcium hydroxide. The resulting product was distilled through a 0.5-meter column and the fraction with a bp 32° C. was drawn off. The content of the basic compound in the collected function was >99%.
2. Isomeric cis- and trans-dichloroethylene (DCE) were prepared by dehydrochlorination of 1,1,2,2-tetrachloroethane with zinc dust in an ethanol solution. The reaction mixture was separated into trans-DCE (bp 47-48° C.) and cis-DCE (bp 60° C.) by rectification.
3. Vinyl chloride (VC) of greater than 99.5% purity was used as received from the supplier.

Part C—Analytical Procedure

The chromatographic analysis of the reaction products was performed on three different columns but at the same flow rate of the carrier gas, 20 ml/min. The columns used are described as follows:

Column A: 3 m long, 4 mm i.d., OV-101 (3 wt. %) on Chromaton N-AW (0.16-0.22 mm), oven temperature 90° C.

Column B: 3 m long, 3 mm i.d., OV-225 (3 wt. %) on Inerton-super (0.16-0.2 mm). The analysis started at 40° C. and then the temperature was raised to 170° C. at the rate of 10° C./min.

Column C: 3 m long, 3 mm i.d., dinonyl phthalate (15 wt. %) on Cheazsorb AW-HMDS (0.25-0.36 mm), oven temperature 70° C.

The retention times of the reaction products measured for each of the columns are reported below in minutes (') and seconds (").

| | Retention time | | | | | |
|---|---|---|---|---|---|---|
| Column | Ethylene | Vinyl chloride | VDC | Trans-DCE | Cis-DCE | TCE |
| A | 4'18" | 4'20" | 4'30" | 5'10" | 6'40" | 15' |
| B | 2'20" | 2'44" | 3'15" | 4'14" | 6'15" | 16' |
| C | 2'30" | 5'30" | 13'50" | 31' | — | — |

Part D—Calculations

The concentration of a particular compound $C_i$ mole/liter) was calculated as the product of the corresponding peak area $A_i$ (mm$^2$) by the response factor $K_i$ (mole/liter.mm$^2$) determined from the calibration curves, based on the formula:

$$C_i = K_i A_i$$

The constancy of the response factor $K_i$ was checked on the starting reaction mixture composed of TCE and nitrogen. The concentration of TCE was calculated from its partial saturation vapor pressure ($P_i$) at a given temperature (t) of the saturator and the pressure (P) in the condenser, according to the following formula:

$$C_v = 100 \, P_i/P(\text{vol. \%}) \text{ or } C = C_v/2240 (\text{mole/l}),$$

wherein $C_v$ and C are the TCE concentrations in terms of volume percentage and mole/liter, respectively. The following equation was used to calculate the partial saturation vapor pressure ($P_i$).

$$\text{Log } P_i = 6.84164 - 1262.6/(t+205).$$

The $K_i$ values for the products (VC, VDC, trans- and cis-DCE) were determined relatively to the $K_i$ for TCE. For this purpose a set of mixtures of the indicated liquid compounds in various proportions was prepared. The mixtures were injected into the chromatographic column with a microsyringe and analyzed. The values of $K_i$ for the products were calculated from the corresponding peak areas in the chromatograms and the concentrations of the compounds in the model mixtures. The ratio $K_{prod}/K_{TCE}$ was found to be practically independent of the composition of the mixtures and was equal to 1.2±0.1, as shown in the following formula:

$$K_{prod} = 1.2 \, K_{TCE}$$

The conversion of TCE, X(%), was estimated by the following formula:

$$X = 100(C'_{TCE} - C_{TCE})/C'_{TCE}$$

wherein $C'_{TCE}$ and $C_{TCE}$ were the concentrations of TCE before and after the reaction.

The selectivity for a particular product $S_i$(%) was calculated according to the following formula:

$$S_i = C_i 100/(C'_{TCE} - C_{TCE}),$$

wherein $C_i$ was the concentration of the product (mol/l).

In the cases where the material balance on carbon was within ±20%, the selectivity for products was determined by the following formula:

$$S_i = C_i 100/\Sigma C_{prod}$$

wherein $\Sigma C_{prod}$ was the sum of the concentrations of the different products.

The balance on carbon δ(%) in TCE and the products was calculated by the following formula $$\delta = 100 - (C'_{TCE} - C_{TCE} - \Sigma C_{prod})100/C'_{TCE}$$

The lower the number was for the balance on carbon, the greater the variability in that particular analysis. A material balance on carbon of 80 or more indicated less variability in the analysis.

Tables 1 thru 6 list the results of Examples 1-6 containing BD-A (2-phenylbenzimidazole) on the synthetic activated carbon SKN-1K: at 20 and 30 weight percent, respectively, in Tables 1 and 2; at 35 weight percent on SKN-3M in Table 3; at 30 weight percent on SKN-M in Table 4; at 20 weight percent on Birch Active Carbon in Table 5 and at 20 weight percent on Kernel Activated Carbon in Table 6. Also note that the concentration of TCE, based on volume in all cases, used in Tables 1 and 2 was about 10%; it was adjusted from 3.6 to 20% in Table 3; it was adjusted from 10.2 to 3.6% in Table 4 and maintained at 10.3 to 10.4 percent in Tables 5 and 6.

TABLE 1

Example 1 - 20 Weight Percent of BD-A on SKN-1K

| Time (hours) | T, °C. | Space velocity, h⁻¹ | Conversion, % | VC | VDC | trans-DCE | cis-DCE | δ, % |
|---|---|---|---|---|---|---|---|---|
| 0.00 | 252 | 163 | 37.6 | 49.2 | 29.4 | 10.3 | 11.1 | 108 |
| 0.30 | 253 | 161 | 31.6 | 34.0 | 38.0 | 15.4 | 12.5 | 100 |
| 0.72 | 220 | 94 | 82.7 | 42.6 | 44.2 | 9.7 | 3.5 | 78 |
| 0.97 | 220 | 94 | 76.5 | 39.5 | 45.0 | 10.7 | 4.8 | 89 |
| 1.33 | 220 | 88 | 78.7 | 39.9 | 42.8 | 11.7 | 5.6 | 76 |
| 1.65 | 220 | 88 | 71.1 | 36.8 | 46.0 | 12.4 | 4.8 | 92 |
| 2.43 | 240 | 95 | 95.3 | 43.5 | 40.1 | 11.1 | 5.3 | 91 |
| 2.60 | 240 | 95 | 96.4 | 40.1 | 41.3 | 12.0 | 6.6 | 99 |
| 2.77 | 240 | 95 | 95.6 | 38.6 | 42.1 | 12.6 | 6.6 | 100 |
| 2.93 | 240 | 95 | 94.9 | 35.9 | 42.6 | 14.1 | 7.3 | 104 |
| 3.97 | 240 | 95 | 94.5 | 29.0 | 45.9 | 16.6 | 8.5 | 97 |
| 4.48 | 240 | 95 | 94.2 | 23.2 | 48.9 | 17.9 | 10.0 | 101 |
| 4.57 | 240 | 105 | 96.5 | 14.1 | 57.6 | 18.9 | 9.4 | 77 |
| 16.13 | 240 | 105 | 76.9 | 10.5 | 47.4 | 24.9 | 17.1 | 90 |
| 16.57 | 240 | 100 | 90.1 | 7.7 | 57.9 | 22.2 | 12.1 | 105 |
| 17.25 | 240 | 97 | 89.8 | 7.4 | 57.0 | 21.9 | 13.7 | 87 |
| 17.42 | 240 | 97 | 93.8 | 6.2 | 57.7 | 23.2 | 12.8 | 105 |
| 17.83 | 240 | 105 | 96.0 | 6.1 | 59.5 | 22.5 | 11.9 | 89 |
| 18.20 | 240 | 97 | 90.2 | 4.8 | 58.9 | 24.0 | 12.3 | 110 |
| 18.50 | 240 | 106 | 90.2 | 4.5 | 58.4 | 24.0 | 13.2 | 110 |
| 19.37 | 240 | 106 | 89.2 | 3.8 | 59.1 | 23.5 | 13.5 | 111 |
| 19.67 | 240 | 1026 | 66.4 | 6.3 | 62.0 | 19.2 | 12.5 | 52 |
| 21.10 | 240 | 1026 | 28.9 | 1.4 | 71.3 | 16.9 | 10.4 | 99 |
| 21.55 | 240 | 1024 | 27.5 | 1.3 | 72.2 | 16.7 | 9.9 | 100 |
| 22.22 | 240 | 105 | 75.9 | 2.0 | 61.6 | 23.2 | 13.3 | 79 |
| 26.42 | 240 | 215 | 62.2 | 1.4 | 61.5 | 22.8 | 14.2 | 139 |
| 27.13 | 240 | 202 | 72.3 | 1.1 | 60.7 | 24.4 | 13.8 | 97 |
| 27.32 | 240 | 202 | 67.5 | 1.3 | 61.0 | 24.4 | 13.3 | 102 |

TABLE 2

Example 2 - 30 Weight Percent of BD-A on SKN-1K

| Time (hours) | T, °C. | Space velocity, h⁻¹ | Conversion, % | VC | VDC | trans-DCE | cis-DCE | δ, % |
|---|---|---|---|---|---|---|---|---|
| 1.23 | 240 | 891 | 28.9 | 1.7 | 78.8 | 11.9 | 7.6 | 97 |
| 1.40 | 240 | 889 | 30.0 | 1.6 | 79.7 | 11.7 | 7.0 | 95 |
| 1.90 | 240 | 898 | 32.0 | 1.4 | 79.4 | 11.9 | 7.2 | 92 |
| 2.10 | 240 | 889 | 32.3 | 1.3 | 79.7 | 11.9 | 7.2 | 92 |
| 3.13 | 240 | 252 | 59.3 | 1.8 | 73.7 | 15.6 | 8.9 | 98 |
| 3.53 | 240 | 260 | 59.3 | 1.8 | 74.8 | 15.0 | 8.4 | 97 |
| 3.72 | 240 | 260 | 59.3 | 2.2 | 75.5 | 14.6 | 7.7 | 96 |
| 4.60 | 240 | 160 | 65.5 | 2.1 | 70.3 | 17.6 | 10.0 | 107 |
| 4.90 | 240 | 160 | 69.2 | 1.6 | 71.4 | 17.6 | 9.4 | 104 |
| 5.73 | 250 | 162 | 86.1 | 2.1 | 69.9 | 17.6 | 10.4 | 104 |
| 5.97 | 250 | 162 | 85.9 | 2.1 | 69.2 | 18.0 | 10.7 | 105 |
| 6.88 | 252 | 148 | 89.6 | 1.6 | 69.5 | 18.3 | 10.6 | 104 |
| 7.15 | 252 | 148 | 87.3 | 1.9 | 69.4 | 18.1 | 10.6 | 110 |
| 7.56 | 252 | 156 | 87.1 | 1.5 | 69.3 | 18.0 | 11.2 | 109 |
| 7.93 | 252 | 147 | 86.3 | 1.4 | 69.3 | 18.1 | 11.2 | 110 |
| 9.48 | 252 | 152 | 89.3 | 1.5 | 68.7 | 18.5 | 11.3 | 95 |
| 9.81 | 252 | 151 | 84.6 | 1.1 | 71.7 | 17.3 | 9.9 | 119 |
| 9.98 | 251 | 151 | 84.7 | 1.4 | 67.9 | 18.8 | 11.9 | 102 |
| 11.15 | 252 | 151 | 84.3 | 1.0 | 71.0 | 17.5 | 10.6 | 107 |
| 11.31 | 250 | 151 | 84.8 | 0.9 | 71.6 | 17.1 | 10.4 | 108 |

TABLE 3

Example 3 - 35 Weight Percent of BD-A on SKN-3M

| Time (hours) | T, °C. | Space Velocity, h⁻¹ | TCE % | Conversion, % | VC | VDC | trans-DCE | cis-DCE | δ, % |
|---|---|---|---|---|---|---|---|---|---|
| 1.1 | 237 | 549 | 3.6 | 49.5 | 2.2 | 87.0 | 7.8 | 3.0 | 88 |
| 1.3 | 238 | 551 | 3.6 | 49.9 | 3.1 | 85.0 | 7.8 | 4.1 | 90 |
| 1.5 | 238 | 551 | 3.6 | 51.9 | 2.7 | 84.0 | 8.9 | 4.4 | 91 |
| 1.9 | 238 | 546 | 3.6 | 54.0 | 2.3 | 83.8 | 8.9 | 4.9 | 82 |
| 2.1 | 238 | 551 | 3.6 | 52.5 | 2.3 | 83.8 | 8.9 | 5.0 | 87 |
| 2.5 | 248 | 574 | 3.6 | 65.9 | 2.7 | 83.9 | 9.0 | 4.4 | 91 |
| 2.7 | 248 | 574 | 3.6 | 65.9 | 2.2 | 84.3 | 8.5 | 5.0 | 94 |
| 3.1 | 254 | 586 | 3.6 | 74.6 | 2.6 | 84.7 | 9.1 | 3.6 | 81 |
| 3.3 | 254 | 589 | 3.6 | 73.5 | 1.9 | 84.8 | 8.9 | 4.4 | 83 |
| 3.8 | 256 | 595 | 3.6 | 76.6 | 1.9 | 85.7 | 8.3 | 4.1 | 84 |
| 5.9 | 257 | 597 | 3.6 | 75.8 | 0.3 | 83.5 | 8.7 | 7.4 | 103 |

TABLE 3-continued

Example 3 - 35 Weight Percent of BD-A on SKN-3M

| Time (hours) | T, °C. | Space Velocity, h⁻¹ | TCE % | Conversion, % | VC | VDC | trans-DCE | cis-DCE | δ, % |
|---|---|---|---|---|---|---|---|---|---|
| 6.1 | 255 | 591 | 3.6 | 74.9 | 0.7 | 87.9 | 8.7 | 2.7 | 97 |
| 6.8 | 252 | 580 | 3.6 | 50.3 | 0.3 | 85.4 | 8.8 | 5.5 | 84 |
| 7.2 | 236 | 549 | 3.6 | 47.3 | 0.3 | 84.3 | 9.2 | 6.2 | 90 |
| 7.8 | 258 | 598 | 3.6 | 79.2 | 1.3 | 84.3 | 9.2 | 5.2 | 89 |
| 8.2 | 262 | 607 | 3.6 | 84.5 | 1.6 | 83.5 | 10.2 | 4.7 | 81 |
| 8.9 | 260 | 678 | 10.1 | 69.9 | 0.7 | 83.5 | 7.7 | 8.1 | 89 |
| 9.1 | 261 | 685 | 10.1 | 65.9 | 1.1 | 81.3 | 11.0 | 6.6 | 93 |
| 9.4 | 260 | 678 | 10.1 | 65.9 | 0.9 | 81.5 | 10.7 | 6.9 | 95 |
| 9.7 | 260 | 672 | 10.2 | 64.6 | 0.8 | 82.5 | 10.6 | 6.0 | 98 |
| 10.1 | 259 | 669 | 10.2 | 60.2 | 0.8 | 81.9 | 10.9 | 6.4 | 98 |
| 10.6 | 260 | 705 | 15.3 | 58.6 | 0.2 | 82.0 | 11.7 | 6.1 | 90 |
| 10.8 | 260 | 705 | 15.3 | 59.6 | 0.2 | 81.3 | 11.7 | 6.8 | 89 |
| 11.7 | 260 | 739 | 20.0 | 53.3 | 0.2 | 80.4 | 12.8 | 6.7 | 90 |

TABLE 4

Example 4 - 30 Weight Percent of BD-A on SKN-M

| Time (hours) | T, °C. | Space Velocity, h⁻¹ | TCE % | Conversion, % | VC | VDC | trans-DCE | cis-DCE | δ, % |
|---|---|---|---|---|---|---|---|---|---|
| 0.72 | 240 | 681 | 10.2 | 39.9 | 10.3 | 71.9 | 11.1 | 6.7 | 91 |
| 1.15 | 240 | 681 | 10.2 | 40.1 | 9.2 | 70.9 | 12.3 | 7.7 | 87 |
| 1.65 | 240 | 686 | 10.2 | 38.6 | 4.7 | 76.9 | 11.5 | 6.9 | 90 |
| 2.17 | 240 | 681 | 10.2 | 36.1 | 3.0 | 78.8 | 11.4 | 6.8 | 93 |
| 3.50 | 238 | 669 | 3.6 | 51.5 | 4.3 | 80.8 | 9.2 | 5.7 | 85 |
| 3.75 | 238 | 668 | 3.6 | 50.5 | 3.3 | 81.6 | 10.1 | 5.0 | 86 |
| 4.18 | 236 | 673 | 3.6 | 48.0 | 3.3 | 81.8 | 10.3 | 4.6 | 84 |
| 5.32 | 236 | 672 | 3.6 | 45.6 | 2.0 | 82.2 | 10.2 | 5.6 | 90 |
| 5.72 | 238 | 669 | 3.6 | 44.8 | 2.0 | 83.2 | 9.6 | 5.3 | 90 |
| 6.13 | 222 | 672 | 3.6 | 32.1 | 1.7 | 85.4 | 9.3 | 3.6 | 87 |
| 6.37 | 222 | 671 | 3.6 | 33.3 | 1.1 | 85.6 | 8.6 | 4.7 | 87 |
| 6.68 | 212 | 667 | 3.6 | 19.8 | 1.3 | 85.6 | 9.2 | 3.9 | 93 |
| 7.47 | 212 | 285 | 3.6 | 22.0 | 1.7 | 81.0 | 11.1 | 6.1 | 110 |
| 8.63 | 204 | 711 | 3.6 | 42.1 | 1.0 | 81.6 | 11.2 | 6.2 | 74 |
| 8.97 | 204 | 710 | 3.6 | 66.3 | 1.2 | 82.2 | 10.3 | 6.3 | 81 |
| 9.42 | 202 | 288 | 3.6 | 38.7 | 1.2 | 81.0 | 11.6 | 6.2 | 75 |
| 10.08 | 203 | 286 | 3.6 | 16.1 | 1.5 | 80.1 | 11.5 | 6.8 | 98 |

TABLE 5

Example 5 - 20 Weight Percent of BD-A on Birch Active Carbon

| Time (hours) | T, °C. | Space Velocity, h⁻¹ | TCE % | Conversion, % | VC | VDC | trans-DCE | cis-DCE | δ, % |
|---|---|---|---|---|---|---|---|---|---|
| 1.4 | 251 | 188 | 10.3 | 78.0 | 9.5 | 72.3 | 11.1 | 7.0 | 89 |
| 1.5 | 251 | 186 | 10.3 | 76.9 | 7.9 | 73.0 | 12.1 | 7.1 | 89 |
| 2.1 | 251 | 185 | 10.3 | 77.0 | 6.8 | 73.9 | 12.2 | 7.1 | 89 |
| 2.5 | 251 | 186 | 10.3 | 77.1 | 5.4 | 74.1 | 12.8 | 7.7 | 92 |
| 3.3 | 251 | 188 | 10.3 | 79.1 | 4.5 | 75.3 | 12.3 | 8.0 | 89 |
| 3.9 | 251 | 182 | 10.3 | 79.4 | 3.8 | 76.1 | 12.2 | 7.9 | 88 |
| 4.3 | 251 | 183 | 10.3 | 78.7 | 4.0 | 75.9 | 12.2 | 7.9 | 91 |
| 4.7 | 251 | 607 | 10.3 | 50.6 | 2.5 | 78.4 | 11.2 | 7.8 | 86 |
| 4.9 | 251 | 605 | 10.3 | 49.0 | 1.9 | 79.6 | 11.4 | 7.2 | 87 |
| 5.6 | 251 | 778 | 10.3 | 44.0 | 1.6 | 83.3 | 9.8 | 5.3 | 89 |
| 5.9 | 251 | 787 | 10.3 | 43.1 | 1.4 | 81.9 | 10.8 | 5.9 | 87 |

TABLE 6

Example 6 - 20 Weight Percent of BD-A on Kernel Active Carbon

| Time (hours) | T, °C. | Space Velocity, h$^{-1}$ | TCE % | Conversion, % | Selectivity, % | | | | δ, % |
|---|---|---|---|---|---|---|---|---|---|
| | | | | | VC | VDC | trans-DCE | cis-DCE | |
| 2.1 | 250 | 188 | 10.3 | 57.7 | 4.3 | 79.6 | 10.8 | 5.4 | 93 |
| 2.6 | 250 | 189 | 10.3 | 52.9 | 4.9 | 76.6 | 10.6 | 7.9 | 95 |
| 2.9 | 250 | 188 | 10.3 | 47.8 | 3.5 | 82.1 | 8.7 | 5.7 | 110 |
| 3.4 | 250 | 188 | 10.4 | 53.9 | 4.9 | 77.1 | 10.7 | 7.2 | 93 |
| 3.9 | 250 | 185 | 10.4 | 53 | 5 | 79.4 | 10.6 | 5.1 | 101 |
| 4.1 | 250 | 185 | 10.4 | 53.0 | 5.0 | 79.4 | 10.6 | 5.1 | 101 |

Tables 7 thru 10 list the results of Examples 7 thru 10 containing BD-B 2-(4-chloro phenyl) benzimidazole at 5, 10, 15 and 20 weight percent, respectively, on the synthetic activated bon SKN-M.

TABLE 7

Example 7 - 5 Weight Percent of BD-B on SKN-M

| Time (hours) | T, °C. | Space Velocity, h$^{-1}$ | TCE % | Conversion, % | Selectivity, % | | | | δ, % |
|---|---|---|---|---|---|---|---|---|---|
| | | | | | VC | VDC | trans-DCE | cis-DCE | |
| 0.7 | 254 | 149 | 10.2 | 99.6 | 8.0 | 44.9 | 30.7 | 16.4 | 79 |
| 1.0 | 254 | 149 | 10.2 | 99.0 | 11.9 | 39.5 | 31.1 | 17.5 | 95 |
| 1.4 | 254 | 150 | 10.2 | 99.4 | 4.4 | 43.9 | 33.8 | 18.0 | 87 |
| 2.0 | 254 | 150 | 10.2 | 99.5 | 3.8 | 43.2 | 33.8 | 19.2 | 90 |
| 3.7 | 254 | 166 | 40.6 | 91.5 | 1.2 | 40.4 | 40.0 | 18.4 | 81 |
| 4.1 | 254 | 169 | 40.7 | 92.2 | 1.0 | 40.1 | 40.5 | 18.4 | 81 |
| 8.1 | 254 | 179 | 40.6 | 94.1 | 0.4 | 38.0 | 42.1 | 19.4 | 79 |

TABLE 8

Example 8 - 10 Weight Percent of BD-B on SKN-M

| Time (hours) | T, °C. | Space Velocity, h$^{-1}$ | TCE % | Conversion, % | Selectivity, % | | | | δ, % |
|---|---|---|---|---|---|---|---|---|---|
| | | | | | VC | VDC | trans-DCE | cis-DCE | |
| 0.9 | 254 | 132 | 10.2 | 98.9 | 13.4 | 54.0 | 18.7 | 13.8 | 105 |
| 1.6 | 254 | 144 | 10.2 | 98.2 | 8.0 | 53.6 | 22.1 | 16.4 | 99 |
| 1.8 | 254 | 146 | 10.2 | 98.0 | 6.8 | 53.0 | 25.1 | 15.1 | 108 |
| 2.4 | 254 | 144 | 10.2 | 97.1 | 2.1 | 57.8 | 23.1 | 17.0 | 98 |
| 2.6 | 254 | 144 | 10.2 | 97.3 | 3.6 | 55.4 | 25.1 | 16.0 | 104 |
| 3.1 | 254 | 248 | 10.2 | 88.5 | 3.3 | 55.9 | 25.8 | 14.9 | 105 |
| 3.2 | 254 | 247 | 10.2 | 88.0 | 3.1 | 55.9 | 24.0 | 17.0 | 107 |
| 3.8 | 254 | 501 | 10.2 | 68.6 | 3.0 | 55.3 | 27.0 | 14.8 | 86 |
| 4.0 | 254 | 504 | 10.2 | 68.8 | 2.4 | 58.0 | 25.3 | 14.3 | 95 |
| 4.7 | 254 | 824 | 10.2 | 61.2 | 2.2 | 60.3 | 23.0 | 14.6 | 84 |
| 4.9 | 254 | 840 | 10.2 | 61.2 | 2.0 | 60.1 | 23.1 | 14.8 | 83 |
| 7.0 | 254 | 54 | 10.2 | 99.9 | 2.1 | 46.4 | 30.9 | 20.6 | 83 |

TABLE 9

Example 9 - 20 Weight Percent of BD-B on SKN-M

| Time (hours) | T, °C. | Space Velocity, h$^{-1}$ | TCE % | Conversion, % | Selectivity, % | | | | δ, % |
|---|---|---|---|---|---|---|---|---|---|
| | | | | | VC | VDC | trans-DCE | cis-DCE | |
| 1.9 | 200 | 80 | 10.3 | 55.9 | 10.5 | 68.9 | 12.3 | 8.2 | 66 |
| 2.2 | 200 | 83 | 10.3 | 55.3 | 8.4 | 64.9 | 14.6 | 12.1 | 84 |
| 4.6 | 236 | 83 | 10.3 | 70.7 | 7.4 | 55.5 | 21.3 | 15.8 | 101 |

TABLE 9-continued

Example 9 - 20 Weight Percent of BD-B on SKN-M

| Time (hours) | T, °C. | Space Velocity, h$^{-1}$ | TCE % | Conversion, % | Selectivity, % VC | VDC | trans-DCE | cis-DCE | δ, % |
|---|---|---|---|---|---|---|---|---|---|
| 5.4 | 234 | 69 | 10.3 | 85.3 | 2.4 | 54.3 | 24.7 | 18.6 | 78 |
| 7.9 | 236 | 66 | 10.3 | 72.7 | 3.1 | 58.6 | 22.2 | 16.1 | 101 |
| 8.3 | 236 | 66 | 10.3 | 72.3 | 3.1 | 57.5 | 22.7 | 16.7 | 110 |
| 8.7 | 252 | 63 | 10.3 | 85.1 | 4.0 | 56.9 | 22.3 | 16.8 | 107 |
| 8.9 | 252 | 63 | 10.3 | 92.6 | 3.6 | 59.9 | 21.1 | 15.4 | 101 |
| 9.7 | 252 | 66 | 10.3 | 93.9 | 3.9 | 59.7 | 21.2 | 15.2 | 104 |
| 12.5 | 265 | 66 | 10.3 | 98.3 | 4.6 | 58.8 | 20.3 | 16.3 | 101 |
| 13.1 | 265 | 70 | 10.3 | 98.3 | 4.6 | 59.8 | 19.8 | 15.9 | 100 |
| 13.4 | 284 | 64 | 10.3 | 99.9 | 5.4 | 51.1 | 23.3 | 20.2 | 93 |
| 13.6 | 284 | 64 | 10.3 | 99.9 | 5.8 | 49.3 | 23.4 | 21.6 | 97 |
| 13.8 | 284 | 64 | 10.3 | 99.9 | 6.8 | 56.8 | 19.9 | 17.5 | 102 |

TABLE 10

Example 10 - 25 Weight Percent of BD-B on SKN-M

| Time (hours) | T, °C. | Space Velocity, h$^{-1}$ | TCE % | Conversion, % | Selectivity, % VC | VDC | trans-DCE | cis-DCE | δ, % |
|---|---|---|---|---|---|---|---|---|---|
| 2.0 | 254 | 159 | 10.2 | 83.6 | 4.5 | 70.3 | 14.3 | 1.9 | 70 |
| 2.8 | 253 | 158 | 10.2 | 84.5 | 4.4 | 67.8 | 15.2 | 12.6 | 72 |
| 3.0 | 253 | 158 | 10.2 | 82.9 | 4.0 | 69.0 | 15.9 | 11.1 | 79 |
| 3.5 | 153 | 158 | 10.2 | 82.8 | 4.8 | 66.6 | 17.2 | 11.5 | 74 |
| 3.5 | 253 | 158 | 10.2 | 85.6 | 3.9 | 64.7 | 16.2 | 15.3 | 63 |
| 4.1 | 255 | 158 | 10.2 | 78.6 | 4.0 | 65.9 | 16.5 | 13.7 | 69 |
| 4.4 | 254 | 139 | 10.2 | 84.6 | 3.9 | 67.0 | 16.8 | 12.3 | 75 |
| 5.9 | 254 | 169 | 10.2 | 81.9 | 4.2 | 66.2 | 16.4 | 13.2 | 81 |
| 6.3 | 254 | 153 | 10.2 | 82.9 | 3.1 | 67.4 | 17.3 | 12.2 | 78 |
| 7.6 | 254 | 161 | 10.2 | 80.1 | 2.4 | 67.2 | 17.5 | 12.9 | 82 |
| 8.6 | 254 | 20 | 10.2 | 99.3 | 5.9 | 66.1 | 16.3 | 11.7 | 70 |
| 9.7 | 254 | 21 | 10.2 | 99.8 | 4.2 | 44.6 | 18.6 | 12.6 | 75 |
| 9.7 | 254 | 34 | 10.2 | 98.7 | 3.5 | 58.4 | 20.6 | 17.5 | 84 |

Table 11 lists the results of Example 11 containing BD-C (2-(4-chlorophenyl-1-methylbenzimidazole on the synthetic activated carbon SKN-M at 20 weight percent. The concentration of TCE was adjusted from 8.7 to 8.8%.

TABLE 11

Example 11 - 20 Weight Percent of BD-C on SKN-M

| Time (hours) | T, °C. | Space Velocity, h$^{-1}$ | TCE % | Conversion, % | Selectivity, % VC | VDC | trans-DCE | cis-DCE | δ, % |
|---|---|---|---|---|---|---|---|---|---|
| 0.5 | 235 | 59 | 8.7 | 96 | 3.4 | 55.8 | 29.3 | 11.5 | 63 |
| 1.5 | 235 | 59 | 8.7 | 81 | 4.1 | 57.7 | 23.4 | 14.7 | 75 |
| 2 | 235 | 59 | 8.7 | 73 | 4.0 | 55.4 | 25.0 | 15.6 | 81 |
| 2.5 | 235 | 59 | 8.7 | 72 | 3.5 | 55.2 | 25.2 | 16.1 | 82 |
| 3.5 | 235 | 59 | 8.8 | 73 | 3.5 | 55.8 | 25.0 | 15.7 | 79 |
| 4 | 235 | 59 | 8.8 | 71 | 3.3 | 55.4 | 25.1 | 16.2 | 82 |
| 5 | 235 | 59 | 8.8 | 72 | 3.2 | 56.3 | 24.8 | 15.7 | 80 |
| 5.5 | 250 | 59 | 8.8 | 85 | 4.3 | 53.2 | 24.8 | 17.8 | 84 |
| 6 | 250 | 59 | 8.8 | 86 | 4.5 | 54.3 | 24.0 | 17.2 | 82 |
| 8.5 | 226 | 60 | 8.9 | 95 | 0.5 | 55.9 | 24.4 | 19.1 | 29 |
| 9 | 226 | 60 | 8.9 | 83 | 0.5 | 54.9 | 26.3 | 18.2 | 50 |
| 10 | 202 | 38 | 8.5 | 81 | 0.8 | 58.9 | 23.2 | 17.1 | 29 |
| 11.5 | 250 | 96 | 8.5 | 77 | 3.2 | 55.9 | 23.6 | 17.0 | 70 |
| 12 | 250 | 96 | 8.5 | 75 | 3.2 | 55.6 | 23.9 | 17.3 | 73 |
| 12.5 | 250 | 144 | 8.5 | 64 | 3.2 | 59.4 | 22.2 | 15.2 | 75 |
| 13 | 250 | 144 | 8.5 | 63 | 3.3 | 57.9 | 22.7 | 16.0 | 79 |

Table 12 lists the results of Example 12 containing BD-D (2-(4-nitrophenyl)benzimidazole) on the synthetic activated carbon SKN-M at 20 weight percent. The concentration of TCE was adjusted from 8.9 to 8.8% after initially being at 6.1%.

TABLE 12

Example 12 - 20 Weight Percent of BD-D on SKN-M

| Time (hours) | T, °C. | Space Velocity, $h^{-1}$ | TCE % | Conversion, % | VC | VDC | trans-DCE | cis-DCE | δ, % |
|---|---|---|---|---|---|---|---|---|---|
| 1.5 | 225 | 90 | 6.1 | 83 | 0.0 | 53.0 | 29.0 | 17.9 | 64 |
| 2.0 | 225 | 90 | 6.1 | 86 | 0.1 | 51.9 | 29.1 | 18.8 | 63 |
| 2.5 | 225 | 90 | 6.1 | 87 | 0.0 | 51.4 | 29.2 | 19.4 | 62 |
| 3.5 | 225 | 190 | 8.9 | 60 | 0.0 | 57.5 | 25.3 | 17.2 | 59 |
| 4.0 | 225 | 190 | 8.9 | 58 | 0.2 | 56.6 | 25.3 | 17.8 | 59 |
| 4.5 | 225 | 190 | 8.9 | 51 | 0.0 | 56.3 | 25.9 | 17.8 | 71 |
| 5.5 | 225 | 118 | 8.9 | 73 | 0.6 | 43.6 | 31.8 | 23.9 | 67 |
| 6.5 | 225 | 118 | 8.9 | 81 | 1.6 | 43.0 | 31.7 | 23.7 | 68 |
| 9.0 | 225 | 110 | 8.9 | 73 | 0.4 | 47.7 | 29.7 | 22.2 | 76 |
| 9.5 | 225 | 110 | 8.9 | 63 | 0.5 | 46.9 | 29.6 | 23.0 | 68 |
| 10.0 | 225 | 110 | 8.9 | 66 | 0.6 | 47.9 | 29.2 | 22.3 | 65 |
| 10.5 | 225 | 227 | 8.9 | 46 | 0.7 | 58.3 | 24.2 | 16.8 | 72 |
| 11.0 | 225 | 227 | 8.9 | 43 | 0.6 | 58.9 | 23.8 | 16.7 | 74 |
| 11.5 | 225 | 227 | 8.9 | 42 | 0.8 | 57.4 | 23.9 | 17.9 | 76 |
| 13.0 | 225 | 160 | 8.9 | 51 | 0.7 | 53.3 | 27.1 | 18.9 | 73 |
| 13.5 | 225 | 160 | 8.9 | 50 | 0.7 | 53.1 | 27.1 | 19.0 | 73 |
| 14.0 | 225 | 108 | 8.9 | 60 | 0.7 | 48.3 | 29.6 | 21.5 | 69 |
| 14.5 | 225 | 108 | 8.9 | 63 | 0.7 | 48.1 | 29.7 | 21.5 | 67 |
| 15.0 | 225 | 67 | 8.9 | 69 | 0.7 | 45.1 | 31.5 | 22.7 | 73 |
| 15.5 | 225 | 67 | 8.9 | 80 | 0.8 | 41.8 | 32.4 | 25.1 | 79 |
| 18.1 | 226 | 144 | 8.9 | 55 | 0.4 | 51.4 | 28.2 | 20.1 | 65 |
| 18.8 | 250 | 144 | 8.9 | 83 | 1.1 | 45.7 | 29.1 | 24.1 | 77 |
| 19.1 | 250 | 144 | 8.9 | 90 | 1.2 | 46.6 | 28.7 | 23.5 | 68 |
| 19.3 | 250 | 144 | 8.9 | 91 | 1.4 | 46.2 | 28.8 | 23.6 | 68 |
| 19.6 | 250 | 144 | 8.9 | 90 | 1.5 | 46.1 | 28.9 | 23.6 | 69 |
| 20.0 | 250 | 331 | 8.9 | 89 | 1.4 | 54.4 | 25.5 | 18.7 | 77 |
| 20.5 | 250 | 331 | 8.9 | 89 | 1.5 | 54.2 | 25.6 | 18.6 | 78 |
| 20.9 | 250 | 331 | 8.9 | 90 | 1.2 | 54.0 | 25.9 | 18.9 | 77 |
| 21.2 | 265 | 331 | 8.9 | 88 | 2.1 | 50.8 | 26.2 | 20.8 | 70 |
| 22.0 | 265 | 331 | 8.9 | 88 | 2.1 | 50.7 | 26.4 | 20.8 | 75 |
| 22.5 | 265 | 331 | 8.9 | 89 | 2.2 | 50.7 | 26.5 | 20.7 | 69 |
| 23.0 | 275 | 331 | 8.9 | 96 | 2.7 | 49.6 | 26.2 | 21.5 | 67 |
| 24.0 | 275 | 331 | 8.9 | 96 | 2.7 | 49.3 | 26.3 | 21.7 | 78 |
| 27.1 | 250 | 98 | 8.8 | 98 | 1.2 | 43.8 | 36.9 | 18.1 | 83 |
| 27.3 | 226 | 98 | 8.8 | 71 | 0.7 | 51.1 | 42.1 | 6.0 | 82 |
| 28 | 226 | 98 | 8.8 | 71 | 0.7 | 50.7 | 42.4 | 6.2 | 83 |

Table 13 lists the results of Example 13 containing BD-E (2-aminomethylbenzimidazole) on the synthetic activated carbon SKN-M at 20 weight percent.

TABLE 13

Example 13 - 20 Weight Percent of BD-E on SKN-M

| Time (hours) | T, °C. | Space Velocity, $h^{-1}$ | TCE % | Conversion, % | VC | VDC | trans-DCE | cis-DCE | δ, % |
|---|---|---|---|---|---|---|---|---|---|
| 1.0 | 208 | 161 | 10.2 | 28.4 | 14.6 | 47.9 | 19.2 | 18.3 | 80 |
| 2.3 | 240 | 237 | 10.2 | 59.5 | 7.6 | 45.4 | 27.9 | 19.0 | 77 |
| 2.7 | 254 | 250 | 10.2 | 71.8 | 8.3 | 43.3 | 28.9 | 19.4 | 80 |
| 3.1 | 254 | 249 | 10.2 | 73.4 | 7.7 | 44.2 | 27.4 | 20.8 | 81 |
| 3.7 | 254 | 249 | 10.2 | 77.9 | 6.5 | 44.2 | 29.4 | 19.9 | 78 |
| 4.2 | 252 | 249 | 10.2 | 70.5 | 4.3 | 40.7 | 30.1 | 25.0 | 100 |
| 7.2 | 252 | 265 | 10.2 | 81.5 | 2.3 | 44.8 | 27.3 | 25.6 | 89 |
| 7.6 | 252 | 264 | 10.2 | 87.4 | 2.3 | 44.3 | 28.2 | 25.2 | 83 |
| 8.9 | 252 | 264 | 10.2 | 84.8 | 2.4 | 43.4 | 29.0 | 25.1 | 95 |
| 9.6 | 226 | 346 | 10.2 | 73.5 | 1.8 | 42.3 | 40.0 | 25.9 | 81 |

Table 14 lists the results of Example 14 containing BD-F (1-methyl-2-(4-methoxyphenyl)benzimidazole) on the synthetic activated carbon SKN-M at 20 weight percent. The concentration of TCE was adjusted from 10.2 to 9.5 to 9.3 to 10.4 to 9.8% during the process run.

TABLE 14

Example 14 - 20 Weight Percent of BD-F on SKN-M

| Time (hours) | T, °C. | Space Velocity, $h^{-1}$ | TCE % | Conversion, % | Selectivity, % | | | | δ, % |
|---|---|---|---|---|---|---|---|---|---|
| | | | | | VC | VDC | trans-DCE | cis-DCE | |
| 0.5 | 239 | 231 | 10.2 | 100 | 25.2 | 53.0 | 12.3 | 9.5 | 76 |
| 1.5 | 239 | 231 | 10.2 | 88 | 21.8 | 55.8 | 12.6 | 9.8 | 79 |
| 2.5 | 239 | 231 | 9.5 | 73 | 14.5 | 58.4 | 15.8 | 11.3 | 82 |
| 3.5 | 239 | 115 | 9.5 | 73 | 16.4 | 53.5 | 18.3 | 11.8 | 76 |
| 4.5 | 239 | 115 | 9.5 | 73 | 12.4 | 53.9 | 19.2 | 14.5 | 74 |
| 5.3 | 253 | 115 | 9.3 | 87 | 13.0 | 54.2 | 19.5 | 13.4 | 89 |
| 6.0 | 253 | 115 | 9.3 | 87 | 12.0 | 55.4 | 19.7 | 13.0 | 88 |
| 6.5 | 250 | 231 | 10.4 | 83 | 9.5 | 55.3 | 20.9 | 14.3 | 87 |
| 7.5 | 250 | 231 | 10.4 | 85 | 9.0 | 56.8 | 20.3 | 13.9 | 81 |
| 8.5 | 250 | 58 | 9.8 | 54 | 7.5 | 62.5 | 18.2 | 11.7 | 74 |
| 9.5 | 250 | 58 | 9.8 | 49 | 7.1 | 61.7 | 19.1 | 12.1 | 82 |
| 10.5 | 250 | 58 | 9.8 | 58 | 6.9 | 59.6 | 20.4 | 13.0 | 79 |

Tables 15 and 16 list the results on TCE at a 10% concentration of Examples 15 and 16 containing BD-G (1,2,4,5-bis (methylimidazo)benzene) on the synthetic activated carbon SKN-M at 20 and 30 weight percent, respectively.

TABLE 15

Example 15 - 20 Weight Percent of BD-G on SKN-3M

| Time (hours) | T, °C. | Space velocity, % $h^{-1}$ | Conversion, % | Selectivity, % | | | | δ, % |
|---|---|---|---|---|---|---|---|---|
| | | | | VC | VDC | trans-DCE | cis-DCE | |
| 0.85 | 242 | 654 | 63.1 | 6.8 | 66.4 | 17.9 | 9.0 | 97 |
| 1.00 | 242 | 654 | 65.6 | 5.2 | 67.7 | 18.8 | 8.2 | 95 |
| 1.38 | 242 | 654 | 68.7 | 4.2 | 65.7 | 20.6 | 9.5 | 93 |
| 2.63 | 242 | 654 | 68.7 | 2.3 | 60.8 | 24.6 | 12.3 | 96 |
| 3.05 | 242 | 653 | 71.5 | 1.9 | 65.8 | 20.2 | 13.1 | 96 |

TABLE 16

Example 16 - 30 Weight Percent of BD-G on SKN-3M

| Time (hours) | T, °C. | Space velocity, % $h^{-1}$ | Conversion, % | Selectivity, % | | | | δ, % |
|---|---|---|---|---|---|---|---|---|
| | | | | VC | VDC | trans-DCE | cis-DCE | |
| 0.65 | 241 | 669 | 62.5 | 1.8 | 76.6 | 14.2 | 7.5 | 72 |
| 0.82 | 241 | 658 | 52.3 | 1.2 | 76.1 | 13.4 | 9.3 | 92 |
| 1.38 | 240 | 658 | 60.3 | 1.7 | 74.9 | 14.8 | 8.6 | 75 |
| 1.68 | 241 | 670 | 64.9 | 1.4 | 73.6 | 15.4 | 9.6 | 73 |
| 2.50 | 242 | 658 | 67.3 | 1.1 | 76.0 | 14.3 | 8.6 | 68 |
| 2.98 | 242 | 658 | 68.4 | 1.2 | 74.9 | 14.3 | 9.6 | 67 |
| 3.43 | 242 | 250 | 92.4 | 0.8 | 70.1 | 17.5 | 11.7 | 79 |
| 3.77 | 243 | 250 | 91.1 | 0.9 | 70.7 | 17.4 | 11.1 | 62 |
| 4.43 | 243 | 250 | 92.6 | 0.8 | 71.0 | 17.5 | 10.8 | 78 |

Table 17 lists the results of the Comparative Example 1 (CE-1) containing BD-A (2-phenylbenzimidazole) on a silica gel. The concentration of TCE was adjusted from 3.6 to 3.8% during the run.

TABLE 17

CE-1 - 20 Weight Percent of BD-A on Silica Gel (KSS)

| Time (hours) | T, °C. | Space Velocity, h⁻¹ | TCE % | Conversion, % | Selectivity, % |  |  |  | δ, % |
|---|---|---|---|---|---|---|---|---|---|
|  |  |  |  |  | VC | VDC | trans-DCE | cis-DCE |  |
| 0.5 | 250 | 120 | 3.6 | 29 | 37.4 | 46.2 | 8.8 | 7.7 | 92 |
| 1.5 | 250 | 120 | 3.6 | 33 | 39.3 | 44.2 | 9.2 | 7.2 | 87 |
| 2.5 | 250 | 120 | 3.6 | 27 | 43.7 | 42.4 | 7.9 | 6.0 | 92 |
| 3.5 | 250 | 120 | 3.6 | 26 | 42.9 | 42.6 | 8.5 | 6.0 | 88 |
| 4.5 | 250 | 120 | 3.6 | 30 | 36.3 | 47.9 | 9.2 | 6.6 | 89 |
| 5.5 | 250 | 120 | 3.6 | 23 | 24.9 | 51.6 | 9.2 | 14.2 | 98 |
| 6.5 | 250 | 120 | 3.6 | 24 | 32.6 | 48.9 | 9.5 | 9.1 | 96 |
| 7.5 | 250 | 120 | 3.6 | 29 | 37.6 | 46.4 | 7.8 | 8.1 | 91 |
| 8.5 | 250 | 98 | 3.8 | 29 | 55.9 | 30.7 | 8.3 | 5.1 | 93 |
| 9.5 | 250 | 98 | 3.8 | 26 | 55.6 | 30.5 | 7.3 | 6.5 | 97 |
| 10.5 | 250 | 98 | 3.8 | 22 | 55.2 | 28.9 | 7.7 | 8.2 | 91 |
| 11.5 | 250 | 98 | 3.8 | 22 | 57.3 | 28.6 | 6.2 | 7.9 | 90 |

Table 18 lists the results of comparative Example 2 (CE-2) comprising SKN-M. The concentration of TCE was adjusted over a range from 7.4 to 13.4% volume during the run.

TABLE 18

SKN-M Synthetic Activated Carbon Support

| No. Run | Catalyst | Time (hours) | T, °C. | Space Velocity, h⁻¹ | TCE % | Conversion, % | Selectivity, % |  |  |  | δ, % |
|---|---|---|---|---|---|---|---|---|---|---|---|
|  |  |  |  |  |  |  | VC | VDC | trans-DCE | cis-DCE |  |
| 1 | SKN-M | 0.7 | 260 | 148 | 9.4 | 100.0 | 0.0 | 24.2 | 51.4 | 2.4 | 91 |
|  |  | 2.5 | 212 | 148 | 9.5 | 100.0 | 0.5 | 27.9 | 51.9 | 19.7 | 86 |
|  |  | 3.3 | 212 | 148 | 9.1 | 93.1 | 0.4 | 27.9 | 52.9 | 18.8 | 96 |
|  |  | 4.1 | 212 | 148 | 8.7 | 96.1 | 0.4 | 28.0 | 52.7 | 18.9 | 95 |
|  |  | 4.8 | 212 | 72 | 8.7 | 97.4 | 0.0 | 28.3 | 52.8 | 18.8 | 96 |
|  |  | 5.8 | 212 | 72 | 8.7 | 96.2 | 0.0 | 27.1 | 53.6 | 19.3 | 96 |
|  |  | 8.9 | 210 | 108 | 7.4 | 75.7 | 0.0 | 27.8 | 54.0 | 18.2 | 99 |
|  |  | 12.2 | 245 | 108 | 8.2 | 99.6 | 0.0 | 24.3 | 52.1 | 23.6 | 92 |
|  |  | 18.2 | 245 | 799 | 8.4 | 100.0 | 0.0 | 25.1 | 56.7 | 18.2 | 91 |
|  |  | 25.1 | 250 | 324 | 8.0 | 100.0 | 0.0 | 25.4 | 53.0 | 21.5 | 85 |
|  |  | 28.6 | 250 | 305 | 13.4 | 97.7 | 0.0 | 26.6 | 55.6 | 17.8 | 86 |
|  |  | 36.2 | 250 | 305 | 13.4 | 99.4 | 0.0 | 25.5 | 55.3 | 19.2 | 85 |

The results of Examples 1-16 listed in Tables 1-16 demonstrated an overall higher result for each example in the percent conversion of TCE and/or the percent selectivity for VDC than the results for Comparative Example 1 having 20 weight percent BD-A on silicas gel, listed in Table 17. The results of each of Examples 1-16 also demonstrated an overall higher percent selectivity for VDC than the results of Comparative Example 2 being SKN-M synthetic activated carbon, listed in Table 18. The results of the embodiments of the present invention were unexpected.

The present invention has been described with reference to specific details of particular embodiments thereof. It is not intended that such details be regarded as limitations upon the scope of the invention except insofar as to the extent that they are included in the accompanying claims.

We claim:

1. A composition adapted to catalyze the vapor phase dehydrohalogenation of 1,1,2-trihaloethane to 1,1-dihaloethylene comprising activated carbon and at least one benzimidazole-containing material.

2. The composition of claim 1 wherein the activated carbon is chosen from a synthetic activated carbon, activated charcoal, activated kernel carbon, activated birch carbon or mixtures thereof.

3. The composition of claim 2 wherein the activated carbon is a synthetic activated carbon comprising from 1 to 8 weight percent of nitrogen.

4. The composition of claim 1 wherein the activated carbon comprises a specific surface area of from 250 to 2000 meters squared per gram.

5. The composition of claim 1 wherein the activated carbon comprises pores of a size equal to or greater than 2 nanometers.

6. The composition of claim 5 wherein the activated carbon comprises pores of a size from 2 to 50 nanometers.

7. The composition of claim 1 wherein the at least one benzimidazole-containing material comprises benzimidazole, derivatives thereof, salts thereof or mixtures thereof.

8. The composition of claim 1 wherein the at least one benzimidazole-containing material comprises an acidity constant (pKa) of at least 10.0 in acetonitrile.

9. The composition of claim 8 wherein the at least one benzimidazoler-containing material comprises an acidity constant (pKa) of from 10.1 to 18.1 in acetonitrile.

10. The composition of claim 7 wherein the at least one benzimidazole-containing material is represented by at least one of the following graphic formulae, salts thereof or mixtures thereof:

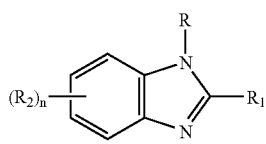

I

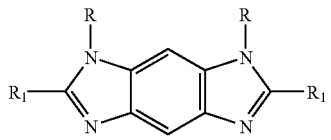

II

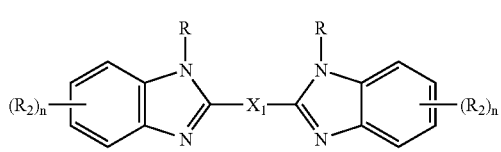

III

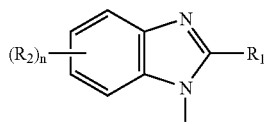

IV

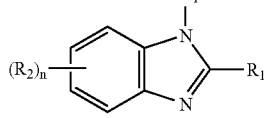

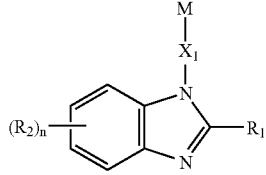

V wherein:

(a) R is chosen from hydrogen, $C_1$-$C_6$ alkyl, $C_1$-$C_6$ haloalkyl, $C_1$-$C_6$ alkoxy($C_1$-$C_4$)alkyl, $C_3$-$C_6$ cycloalkyl, mono($C_1$-$C_6$)alkoxy($C_3$-$C_6$)-cycloalkyl, mono($C_1$-$C_6$) alkyl($C_3$-$C_6$)cycloalkyl, halo($C_3$-$C_6$)cycloalkyl, —N($R_4$)$R_5$, —($C_1$-$C_6$)alkylene-N($R_4$)$R_5$ or —($C_1$-$C_6$) alkylene-oxy-N($R_4$)$R_5$, wherein $R_4$ and $R_5$ are each independently chosen for each occurrence from hydrogen, $C_1$-$C_6$ alkyl, $C_1$-$C_6$ alkoxy, $C_5$-$C_7$ cycloalkyl, $C_6$-$C_{20}$ bicycloalkyl, $C_7$-$C_{20}$ tricycloalkyl, mono($C_1$-$C_6$)alkylamino($C_1$-$C_6$)alkylene, di($C_1$-$C_6$)alkylamino ($C_1$-$C_6$)alkylene, aryl, furanyl, thienyl, $C_1$-$C_6$ alkoxyalkyl, mono-substituted and di-substituted aryl, or $R_4$ and $R_5$ together with the nitrogen atom form an unsubstituted, mono-substituted or di-substituted heterocyclic ring chosen from pyridyl, quinolyl, isoquinolyl, indolinyl, morpholino, pyrimidinyl, piperidino, pyrrolidyl, imidazolidyl, imidazolinyl, pyrazolidyl, pyrazolinyl, piperazinyl, pyrryl, $C_6$-$C_{20}$ heterobicycloalkyl or, $C_7$-$C_{20}$ heterotricycloalkyl, each of said aryl and heterocyclic ring substituents being chosen from halo, amino, mono($C_1$-$C_6$)alkylamino, di($C_1$-$C_6$)alkylamino, amino ($C_1$-$C_6$)alkylene, mono($C_1$-$C_6$)alkylamino($C_1$-$C_6$)alkylene, di($C_1$-$C_6$)alkylamino($C_1$-$C_6$)alkylene, $C_1$-$C_6$ alkyl or $C_1$-$C_6$ alkoxy;

(b) $R_1$ is chosen from:

(i) hydrogen, $C_1$-$C_6$ alkyl, $C_1$-$C_6$ haloalkyl, $C_1$-$C_6$ alkoxy($C_1$-$C_6$)alkyl, $C_1$-$C_6$ alkyl($C_1$-$C_6$)alkoxy, aryloxy($C_1$-$C_6$)alkyl, aryl($C_1$-$C_6$)alkyl, haloaryl($C_1$-$C_6$) alkyl, aryl($C_1$-$C_6$)alkoxy, haloaryl($C_1$-$C_6$)alkoxy, $C_3$-$C_6$ cycloalkyl, mono($C_1$-$C_6$)alkoxy($C_3$-$C_6$)cycloalkyl, mono($C_1$-$C_6$)alkyl($C_3$-$C_6$)cycloalkyl, halo ($C_3$-$C_6$)cycloalkyl, —($C_1$-$C_6$)alkylene-N($R_4$)$R_5$, —($C_1$-$C_6$)alkylene-oxy-N($R_4$)$R_5$ or —N($R_4$)$R_5$; or (ii) unsubstituted, mono-, di-, or tri-substituted aryl groups, phenyl or naphthyl, each of said aryl substituents being chosen from —N($R_4$)$R_5$, hydroxy, aryl, mono($C_1$-$C_6$)alkoxyaryl, di($C_1$-$C_6$)alkoxyaryl, mono ($C_1$-$C_6$)alkylaryl, $C_1$-$C_6$ alkoxy ($C_1$-$C_6$)alkoxy, di($C_1$-$C_6$)alkylaryl, haloaryl, $C_3$-$C_7$ cycloalkylaryl, $C_3$-$C_7$ cycloalkyl, $C_3$-$C_7$ cycloalkyloxy, $C_3$-$C_7$ cycloalkyloxy($C_1$-$C_6$)alkyl, $C_3$-$C_7$ cycloalkyloxy ($C_1$-$C_6$)alkoxy, aryl($C_1$-$C_6$)alkyl, aryl($C_1$-$C_6$)alkoxy, aryloxy, aryloxy($C_1$-$C_6$)alkyl, aryloxy($C_1$-$C_6$)alkoxy, mono- or di-($C_1$-$C_6$)alkylaryl($C_1$-$C_6$)alkyl, mono- or di-($C_1$-$C_6$)alkoxyaryl($C_1$-$C_6$)alkyl, mono- or di-($C_1$-$C_6$)alkylaryl($C_1$-$C_6$)alkoxy, mono- or di-($C_1$-$C_6$) alkoxyaryl($C_1$-$C_6$)alkoxy, $C_1$-$C_6$ alkyl, $C_1$-$C_6$ haloalkyl, $C_1$-$C_6$ alkoxy, mono($C_1$-$C_6$)alkoxy($C_1$-$C_4$) alkyl, halogen, —$SR_3$, or —$S(0)R_3$; wherein $R_3$ is chosen from —N($R_4$)$R_5$, $C_1$-$C_6$ alkyl, phenyl($C_1$-$C_3$) alkyl, mono($C_1$-$C_6$)alkyl substituted phenyl($C_1$-$C_3$) alkyl, mono($C_1$-$C_6$)alkoxy substituted phenyl($C_1$-$C_3$) alkyl or an unsubstituted, mono- or di-substituted aryl group wherein each of said aryl group substituents of $R_3$ being independently chosen from —N($R_4$)$R_5$, $C_1$-$C_6$ alkyl or $C_1$-$C_6$ alkoxy;

(c) each $R_2$ is independently chosen for each occurrence from: R or $R_1$ and n is the integer 0, 1, 2, 3 or 4;

(d) $X_1$ is chosen from —($CH_2$)$_t$—; —O—($CH_2$)$_t$—; or —O—($CH_2$)$_t$—O—; wherein t is the integer 1, 2, 3, 4, 5 or 6; or the group T represented by the formula:

—Z[($OC_2H_4$)$_a$($OC_3H_6$)$_b$($OC_4H_8$)$_c$]Z or

—[($OC_2H_4$)$_a$($OC_3H_6$)$_b$($OC_4H8$)$_c$]— wherein —Z is —C(O)— or —$CH_2$—, a, b and c are each a number between 0 and 50, and the sum of a, b and c is between 2 and 50; and x and y are each independently chosen for each occurrence from 2, 3 or 4; and (e) M is chosen from hydroxy, acryloxy, methacryloxy, 2-(acryloxy)ethyl carbamyl, 2-(methacryloxy)ethylcarbamyl, epoxy, vinyl, allyl or tri($C_1$-$C_6$)alkoxysilyl.

11. The composition of claim 10 wherein the at least one benzimidazole-containing material is represented by at least one of the following graphic formulae I or III:

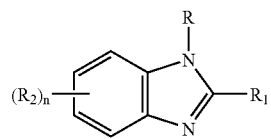

I

-continued

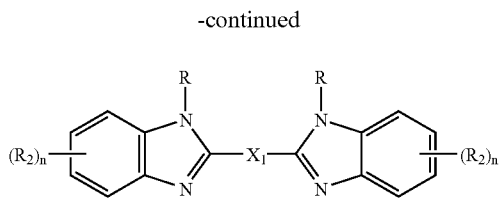

III wherein:
(a) R is chosen from hydrogen, $C_1$-$C_6$ alkyl, $C_1$-$C_6$ haloalkyl, halo($C_3$-$C_6$)cycloalkyl, —N($R_4$)$R_5$, —($C_1$-$C_6$)alkylene-N($R_4$)$R_5$ or —($C_1$-$C_6$)alkylene-oxy-N($R_4$)$R_5$, wherein $R_4$ and $R_5$ are each independently chosen for each occurrence from hydrogen, $C_1$-$C_6$ alkyl, mono($C_1$-$C_6$)alkylamino($C_1$-$C_6$)alkylene, di($C_1$-$C_6$)alkylamino($C_1$-$C_6$)alkylene, aryl, furanyl, thienyl, mono-substituted or di-substituted aryl, or $R_4$ and $R_5$ together with the nitrogen atom form an unsubstituted or mono-substituted heterocyclic ring chosen from pyridyl, quinolyl, isoquinolyl, morpholino or piperidino, each of said aryl and heterocyclic ring substituents being chosen from halo, amino, mono($C_1$-$C_6$)alkylamino, di($C_1$-$C_6$)alkylamino, amino($C_1$-$C_6$)alkylene, mono($C_1$-$C_6$)alkylamino($C_1$-$C_6$)alkylene, di($C_1$-$C_6$)alkylamino($C_1$-$C_6$)alkylene, $C_1$-$C_6$ alkyl or $C_1$-$C_6$ alkoxy;
(b) $R_1$ is chosen from:
  (i) hydrogen, $C_1$-$C_6$ alkyl, $C_1$-$C_6$ haloalkyl, aryloxy($C_1$-$C_6$)alkyl, halo($C_3$-$C_6$)cycloalkyl, —($C_1$-$C_6$)alkylene-N($R_4$)$R_5$, —($C_1$-$C_6$)alkylene-oxy-N($R_4$)$R_5$ or —N($R_4$)$R_5$; or
  (ii) unsubstituted, mono-, or di-substituted aryl groups, phenyl or naphthyl, each of said aryl substituents being chosen from —N($R_4$)$R_5$, aryl, mono($C_1$-$C_6$)alkoxyaryl, di($C_1$-$C_6$)alkoxyaryl, mono($C_1$-$C_6$)alkylaryl, di($C_1$-$C_6$)alkylaryl, haloaryl, $C_3$-$C_7$ cycloalkylaryl, aryloxy, $C_1$-$C_6$ alkyl, $C_1$-$C_6$ haloalkyl, $C_1$-$C_6$ alkoxy, halogen, or —S$R_3$; wherein $R_3$ is chosen from —N($R_4$)$R_5$, $C_1$-$C_6$ alkyl, or an unsubstituted, or mono-substituted aryl group wherein each of said aryl group substituents of $R_3$ being independently chosen from —N($R_4$)$R_5$, $C_1$-$C_6$ alkyl or $C_1$-$C_6$ alkoxy;
(c) each $R_2$ is independently chosen for each occurrence from: R or $R_1$ and n is the integer 0, 1, 2 or 3;
(d) $X_1$ is chosen from —(CH$_2$)$_t$—; wherein t is the integer 1, 2, 3, 4, 5 or 6.

12. The composition of claim 11 wherein:
(a) R is chosen from hydrogen, $C_1$-$C_3$ alkyl, $C_1$-$C_3$ haloalkyl, or —N($R_4$)$R_5$, wherein $R_4$ and $R_5$ are each independently chosen for each occurrence from hydrogen or $C_1$-$C_3$ alkyl or $R_4$ and $R_5$ together with the nitrogen atom form an unsubstituted or mono-substituted heterocyclic ring chosen from pyridyl, quinolyl, isoquinolyl, morpholino or piperidino, each of said aryl and heterocyclic ring substituents being chosen from chloro, fluoro, amino, mono($C_1$-$C_3$)alkylamino, or di($C_1$-$C_3$)alkylamino;
(b) $R_1$ is chosen from:
  (i) hydrogen $C_1$-$C_3$ alkyl, $C_1$-$C_3$ haloalkyl, halo($C_3$-$C_6$)cycloalkyl, phenoxy($C_1$-$C_3$)alkyl, naphthoxy ($C_1$-$C_3$) alkyl, —($C_1$-$C_3$)alkylene-N($R_4$)$R_5$, —($C_1$-$C_3$)alkylene-oxy-N($R_4$)$R_5$ or —N($R_4$)$R_5$; or
  (ii) unsubstituted, or mono-substituted aryl groups, phenyl or naphthyl, each of said aryl substituents being chosen from —N($R_4$)$R_5$, aryl, $C_1$-$C_3$ alkyl, $C_1$-$C_3$ haloalkyl, $C_1$-$C_3$ alkoxy, chloro or fluoro;
(c) each $R_2$ is independently chosen for each occurrence from: R or $R_1$ and n is the integer 0,1 or 2; and
(d) $X_1$ is chosen from —(CH$_2$)$_t$—; wherein t is the integer 1, 2 or 3.

13. The composition of claim 1 wherein the at least one benzimidazole-containing material is chosen from:
  a) 2-phenylbenzimidazole;
  b) 2-(4-chlorophenyl)benzimidazole;
  c) 2-(4-chlorophenyl)-1-methylbenzimidazole;
  d) 1-methyl-2-(4-methoxyphenyl)benzimidazole;
  e) 1,2,4,5-bis(methylimidazo)benzene;
  f) 2-(4-tolyl)benzimidazole;
  g) 2-(4-pyridyl)benzimidazole;
  h) 2-ethyl-1-methylbenzimidazole;
  i) 1-methyl-2-(4-tolyl)benzimidazole;
  j) 2-methylbenzimidazole;
  k) bis(2-benzimidazolyl)methane;
  l) 1,2,4,5-bis(methylimidazo)benzene;
  m) benzimidazole;
  n) 2-(phenoxymethyl)benzimidazole;
  o) 2-(2-naphthoxymethyl)benzimidazole;
  p) 2-(4-dimethylaminophenyl)benzimidazole;
  q) salts thereof; or
  r) mixtures thereof.

14. The composition of claim 1 wherein the composition is adapted to catalyze the vapor phase dehydrohalogenation of 1,1,2-trichloroethane to 1,1-dichloroethylene.

15. A method for dehydrohalogenating 1,1,2-trihaloethane to 1,1-dihaloethylene comprising:
  a) obtaining an activated carbon comprising a catalytic amount of at least one benzimidazole-containing material;
  b) obtaining a vapor phase of 1,1,2-trihaloethane; and
  c) contacting (a) with (b) to form reaction products comprising 1,1-dihaloethylene.

16. The method of claim 15 for dehydrohalogenating 1,1,2-trihaloethane to 1,1-dihaloethylene further comprising:
  d) recovering 1,1-dihaloethylene from (c).

17. The method of claim 15 wherein b) comprises a non-reactive diluent.

18. The method of claim 15 wherein the vapor phase of 1,1,2-trihaloethane in b) is maintained at a temperature of from 114° C. to 300° C.

19. The method of claim 15 wherein the contacting of (a) with (b) to form reaction products comprising 1,1-dialoethylene comprises from 0.1 second to 3,600 seconds.

20. The method of claim 15 wherein the method is for the dehydrohalogenation of 1,1,2-trichloroethane to 1,1-dichloroethylene.

21. A method for producing a composition adapted to catalyze the dehydrohalogenation of 1,1,2-trihaloethane to 1,1-dihaloethylene comprising:
  a) obtaining an activated carbon; and
  b) introducing at least one benzimidazole-containing material into said activated carbon.

22. The method of claim 21 further comprising c) dissolving the at least one benzimidazole-containing material in solvent prior to introducing said benzimidazole-containing material into the activated carbon.

23. The method of claim 22 wherein said solvent in c) is chosen from water, acetone, acetonitrile, ethanol, propanol, methylane chloride, n-methylpyrrolidinones dioxane, chloroform, nitromethane, benzene, toluene, methyl ethyl ketone, methyl isobutyl ketone, isopropyl alcohol, propylene carbonate, 2-methoxyethyl ether, xylene, cyclohexane, 3-methyl cyclohexanone, ethyl acetate, butyl acetate, tetrahydroduran, amyl propionate, methyl propionate, propylene glycol methyl ether, dimethyl sulfoxide, dimethyl formamide, diethylene glycol dibenzoate, dialkyl ethers of ethylene glycol, dimethyl ether, dimethyl ether derivates, or mixtures thereof.

24. The method of claim 21 wherein the method is for producing material adapted to catalyze the dehydrohalogenation of 1,1,2-trichloroethane to 1,1-dichloroethylene.

* * * * *